United States Patent
Wilson et al.

(10) Patent No.: US 10,322,159 B2
(45) Date of Patent: *Jun. 18, 2019

(54) METHODS FOR THE PREVENTION OR TREATMENT OF NO-REFLOW FOLLOWING ISCHEMIA/REPERFUSION INJURY

(71) Applicants: Stealth BioTherapeutics Corp., Monaco (MC); Good Samaritan Institute for Research and Education, Los Angeles, CA (US)

(72) Inventors: D. Travis Wilson, Newton, MA (US); Kenneth Borow, Bryn Mawr, PA (US); Robert A. Kloner, Toluca Lake, CA (US); Sharon Hale, Los Angeles, CA (US)

(73) Assignees: STEALTH BIOTHERAPEUTICS CORP, Monaco (MC); GOOD SAMARITAN INSTITUTE FOR RESEARCH AND EDUCATION, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/158,005

(22) Filed: May 18, 2016

(65) Prior Publication Data

US 2017/0087204 A1 Mar. 30, 2017

Related U.S. Application Data

(63) Continuation of application No. 13/808,027, filed as application No. PCT/US2011/043424 on Jul. 8, 2011, now Pat. No. 9,345,738.

(60) Provisional application No. 61/363,129, filed on Jul. 9, 2010, provisional application No. 61/363,133, filed on Jul. 9, 2010, provisional application No. 61/412,655, filed on Nov. 11, 2010.

(51) Int. Cl.
| | | |
|---|---|---|
| *A61K 38/07* | (2006.01) | |
| *A61P 9/10* | (2006.01) | |
| *A61K 38/00* | (2006.01) | |
| *A61K 45/06* | (2006.01) | |

(52) U.S. Cl.
CPC .............. *A61K 38/07* (2013.01); *A61K 38/00* (2013.01); *A61K 45/06* (2013.01)

(58) Field of Classification Search
None
See application file for complete search history.

(56) References Cited

U.S. PATENT DOCUMENTS

| | | |
|---|---|---|
| 4,522,811 A | 6/1985 | Eppstein et al. |
| 5,674,534 A | 10/1997 | Zale et al. |
| 5,716,644 A | 2/1998 | Zale et al. |

FOREIGN PATENT DOCUMENTS

| | | |
|---|---|---|
| CN | 101296704 A | 10/2008 |
| JP | H05-301868 | 11/1993 |
| JP | 06-507170 | 8/1994 |
| JP | 2007-518818 | 7/2007 |
| WO | WO-92/19250 | 11/1992 |
| WO | WO-96/40073 | 12/1996 |
| WO | WO-99/15154 | 4/1999 |
| WO | WO-00/38651 | 7/2000 |
| WO | WO-2004/013173 | 2/2004 |
| WO | WO-2005/072295 A2 | 8/2005 |
| WO | WO-2007/035640 A2 | 3/2007 |

OTHER PUBLICATIONS

Braunwald et al., "Myocardial reperfusion: a double-edged sword?," J. Clin. Invest. 76: 1713-1719 (1985).*
Toombs, "New directions in thrombolytic therapy," Curr. Opin. Pharmacol. 1:164-168 (2001).*
Szeto, "Cell-permeable, Mitochondrial-targeted, Peptide Antioxidants," AAPS J. 8: E277-E283 (2006).*
Notification of Reexamination issued on Chinese Application 201180042936.5, dated Mar. 29, 2017, English translation only.
Office Action issued on Japanese Application 2016136149, dated May 1, 2017, English Translation only.
"Distal Protection Device", (2005), vol. 53, No. 5, pp. 489-495—In Japanese.
Akasaka, Takashi et al., "Relation of Phasic Coronary Flow Velocity Characteristics with TIMI Perfusion Grade and Myocardial Recovery After Primary Percutaneous Transluminal Coronary Angioplasty and Rescue Stenting," Circulation, (2000), 101, pp. 2361-2367.
Ali, Arshad, "Rheolytic thrombectomy in patients with acute MI did not result in a reduction in myocardial infarct," Presented at Transcatheter Cardiovascular Therapeutics, Sep. 27 to Oct. 1, 2004, in Washington, DC.
Allen, Diane M. et al., "Pathophysiology and related studies of the no-reflow phenomenon in skeletal muscle," Clin Orthop., (May 1995), No. 314, pp. 122-133.
Ames III, Adelbert et al., "Cerebral Ischemia, II. The No-Reflow Phenomenon," Am. J. Pathol., (Feb. 1968), vol. 52, No. 2, pp. 437-447.
Amselem, S., "Liposome Technology," (1993), vol. 1, 2nd Ed. CRC Press, (26 pages).
Asano, Takao et al., "Pathogenetic role of no-reflow phenomenon in experimental subarachnoid hemorrhage in dogs," J Neurosurg., (Apr. 1977), vol. 46, No. 4, pp. 454-466.
Bolognese, Leonardo et al., "Impact of Microvascular Dysfunction on Left Ventricular Remodeling and Long-Term Clinical Outcome After Primary Coronary Angioplasty for Acute Myocardial Infarction," Circulation, (Mar. 9, 2004), vol. 109, pp. 1121-1126.
Cai, Zheqing et al., "Phosphatidylinositol-3-Kinase Signaling is Required for Erythropoietin-Mediated Acute Protection Against Myocardial Ischemia/Reperfusion Injury," Circulation, (May 4, 2004), vol. 109, pp. 2050-2053.

(Continued)

*Primary Examiner* — Julie Ha
*Assistant Examiner* — Kristina M Hellman
(74) *Attorney, Agent, or Firm* — Foley & Lardner LLP

(57) ABSTRACT

The invention provides methods of preventing or treating cardiac ischemia-reperfusion injury in a mammalian subject. The methods provide administering aromatic-cationic peptides in effective amounts to prevent or treat an anatomic zone of no re-flow in mammalian subjects. The methods comprise administering to the subject an effective amount of an aromatic-cationic peptide to subjects in need thereof.

11 Claims, 10 Drawing Sheets

(56) References Cited

OTHER PUBLICATIONS

Cerisoli, M. et al., "Experimental cerebral «no-reflow phenomenon». Response to intracarotid injection of dexamethasone, furosemide and escina," J Neurosurg Sci., (1981), 25, pp. 7-12.
Chait, Laurence A. et al., "The effects of the perfusion of various solutions on the no-reflow phenomenon in experimental free flaps," Plast Reconstr Surg., (Mar. 1978), vol. 61, No. 3, pp. 421-430.
Cho, Sunghee et al., "A Novel Cell-permeable Antioxidant Peptide, SS31, Attenuates Ischemic Brain Injury by Down-regulating CD36," J. Biol. Chem., (Feb. 2007), vol. 282, No. 7, pp. 4634-4642.
Chonn, Arcadio et al., "Recent Advances in Liposomal Drug-Delivery Systems," Current Opinion in Biotechnology, (1995), vol. 6, pp. 698-708.
Claeys, Marc J. et al., "Determinants and Prognostic Implications of Persistent ST-Segment Elevation After Primary Angioplasty for Acute Myocardial Infarction: Importance of Microvascular Reperfusion Injury on Clinical Outcome," Circulation, (Apr. 20, 1999), vol. 99, pp. 1972-1977.
Coggins, Matthew P. et al., "Noninvasive Prediction of Ultimate Infarct Size at the Time of Acute Coronary Occlusion Based on the Extent and Magnitude of Collateral-Derived Myocardial Blood Flow," Circulation, (Nov. 13, 2001), vol. 104, pp. 2471-2477.
Decision of Rejection received for Chinese Patent Application No. 201180042936.5 dated Apr. 19, 2016, 9 pages with English translation.
Eeckhout, E. et al., "The coronary no-reflow phenomenon: a review of mechanisms and therapies," European Heart Journal, (May 2001), vol. 22, Issue 9, pp. 729-739.
Extended Search Report received in European Application No. 11804436.1 dated Dec. 12, 2013 (6 pages).
Final Office Action received for U.S. Appl. No. 13/808,027 dated Jan. 27, 2015, 16 pages.
Final Rejection received for Japanese Patent Application No. 2013-518868 dated Mar. 9, 2016, 3 pages with English translation.
First Examination Report received for European Patent Application No. 11804436.1 dated Aug. 3, 2016, 5 pages.
First Office Action received in Chinese Patent Application No. 201180042936.5 dated Feb. 21, 2014—with English Translation (14 pages).
Fuster, Valentin et al., "The Pathogenesis of Coronary Artery Disease and the Acute Coronary Syndromes," N Engl J Med, (Jan. 23, 1992), vol. 326, No. 4, pp. 242-250.
Gibson, C. Michael et al., "Relationship of TIMI Myocardial Perfusion Grade to Mortality After Administration of Thrombolytic Drugs," Circulation, (2000), 101, pp. 125-130.
Gick, Michael et al., "Randomized Evaluation of the Effects of Filter-Based Distal Protection on Myocardial Perfusion and Infarct Size After Primary Percutaneous Catheter Intervention in Myocardial Infarction With and Without ST-Segment Elevation," Circulation, (Sep. 6, 2005), vol. 112, pp. 1462-1469.
Gregoriadis, G., "Engineering Liposomes for Drug Delivery: Progress and Problems," Trends in Biotechnology, (Dec. 1995), vol. 13, No. 12, pp. 527-537.
Grines, Cindy L. et al., "Coronary Angioplasty with or without Stent Implantation for Acute Myocardial Infarction," New England Journal of Medicine, (Dec. 23, 1999), vol. 341, No. 26, pp. 1949-1956.
Hori, M. et al., "Role of adenosine in hyperemic response of coronary blood flow in microembolization," Am J Physiol, (Mar. 1, 1986), vol. 250, No. 3, pp. H509-H518.
International Search Report and Written Opinion of the ISA for Application No. PCT/US2011/043424 dated Sep. 13, 2011 (10 pages).
Ishii, Hideki et al., "Impact of a Single Intravenous Administration of Nicorandil Before Reperfusion in Patients with ST-Segment-Elevation Myocardial Infarction," Circulation, (Aug. 30, 2005), vol. 112, pp. 1284-1288.
Ito, Hiroshi et al., "Clinical Implications of the 'No Reflow' Phenomenon: A Predictor of Complications and Left Ventricular Remodeling in Reperfused Anterior Wall Myocardial Infarction," Circulation, (Jan. 15, 1996), vol. 93, No. 2, pp. 223-228.
Ito, Hiroshi et al., "Intravenous Nicorandil Can Preserve Microvascular Integrity and Myocardial Viability in Patients with Reperfused Anterior Wall Myocardial Infarction," J Am Coll Cardiol, (Mar. 1, 1999), vol. 33, No. 3, pp. 654-660.
Ito, Hiroshi et al., "Lack of Myocardial Perfusion Immediately After Successful Thrombolysis: A Predictor of Poor Recovery of Left Ventricular Function in Anterior Myocardial Infarction," Circulation, (May 1992), vol. 85, No. 5, pp. 1699-1705.
Ito, Hiroshi et al., "Myocardial perfusion patterns related to thrombolysis in myocardial infarction perfusion grades after coronary angioplasty in patients with acute anterior wall myocardial infarction," Circulation, (Jun. 1, 1996), vol. 93, No. 11, pp. 1993-1999.
Ito, Hiroshi, "No-reflow phenomenon and prognosis in patients with acute myocardial infarction," Nature Clinical Practice: Cardiovascular Medicine, (Sep. 2006), vol. 3, No. 9, pp. 499-506.
Ito, Umeo et al., "Transient Appearance of "No-Reflow" Phenomenon in Mongolian Gerbils," Stroke, (Sep.-Oct. 1980), vol. 11, No. 5, pp. 517-521.
Iwakura, Katsuomi et al., "Alternation in the Coronary Blood Flow Velocity Pattern in Patients with No Reflow and Reperfused Acute Myocardial Infarction," Circulation, (Sep. 15, 1996), vol. 94, No. 6, pp. 1269-1275.
Iwakura, Katsuomi et al., "Association Between Hyperglycemia and the No-Reflow Phenomenon in Patients With Acute Myocardial Infarction," J Am Coll Cardiol, (Jan. 1, 2003), vol. 41, No. 1, pp. 1-7.
Iwakura, Katsuomi et al., "Predictive Factors for Fevelopment of the No-Reflow Phenomenon in Patients With Reperfused Anterior Wall Acute Myocardial Infarction," J Am Coll Cardiol, (Aug. 2001), vol. 38, No. 2, pp. 472-477.
Johnston, William H. et al., "Glomerular Mesangial and Endothelial Cell Swelling Following Temporary Renal Ischemia and Its Role in the No-Reflow Phenomenon," Am J Pathol., (Oct. 1977), vol. 89, No. 1, pp. 153-166.
Kloner, Robert A. et al., "The "No-Reflow" Phenomenon after Temporary Coronary Occlusion in the Dog," J Clin Invest, (Dec. 1974), vol. 54, pp. 1496-1508.
Kloner, Robert A. et al., "Ultrastructural Evidence of Microvascular damage and myocardial cell injury after coronary artery occlusion: which comes first?" Circulation, (Nov. 1980), vol. 62, No. 5, pp. 945-952.
Kocher, A.A. et al., "Neovascularization of ischemic myocardium by human bone-marrow-derived angioblasts prevents cardiomyocyte apoptosis, reduces remodeling and improves cardiac function," Nat Med, (Apr. 2001), vol. 7, No. 4, pp. 430-436.
Komamura, Kazuo et al., "Progressive decreases in coronary vein flow during reperfusion in acute myocardial infarction: clinical documentation of the no reflow phenomenon after successful thrombolysis," J Am Coll Cardiol, (Aug. 1994), vol. 24, No. 2, pp. 370-377.
Kotani, Jun-ichi et al., "Plaque gruel of atheromatous coronary lesion may contribute to the no-reflow phenomenon in patients with acute coronary syndrome," Circulation, (Sep. 24, 2002), vol. 106, pp. 1672-1677.
Kozarich, John W. et al., "Next generation therapeutics: Looking to the horizon: Editorial overview," Current Opinion in Chemical Biology, (1998), vol. 2, Issue 4, pp. 439-440.
Kunichika, Hideki et al., "Effects of glycoprotein IIb/IIIa inhibition on microvascular flow after coronary reperfusion. A quantitative myocardial contrast echocardiography study," J Am Coll Cardiol, (Jan. 21, 2004), vol. 43, No. 2, pp. 276-283.
Lichtenberg, Dov et al., "Liposomes: Preparation, Characterization, and Preservation," Methods Biochem. Anal., (1998), vol. 33, pp. 337-462.
Majno, Guido et al., "No-reflow after cerebral ischaemia," Lancet., (Sep. 9, 1967), vol. 2, pp. 569-570.
Makaryus, Amgad N. et al., "Efficacy of Rheolytic Thrombectomy in Early Versus Late Myocardial Infarction," J Intery Cardiol, (2006), vol. 19, No. 2, pp. 135-140.
Malmberg, Klas et al., "Glycometabolic state at admission: important risk marker of mortality in conventionally treated patients with diabetes mellitus and acute myocardial infarction: long-term results

(56) References Cited

OTHER PUBLICATIONS from the Diabetes and Insulin-Glucose Infusion in Acute Myocardial Infarction (DIGAMI) study," Circulation, (May 25, 1999), vol. 99, pp. 2626-2632.

Manciet, Lorraine H. et al., "Microvascular compression during myocardial ischemia: mechanistic basis for no-reflow phenomenon," Am J Physiol, (Apr. 1, 1994), vol. 266, No. 4 pp. H1541-H1550.

Marzilli, Mario et al., "Beneficial effects of intracoronary adenosine as an adjunct to primary angioplasty in acute myocardial infarction," Circulation, (May 9, 2000), vol. 101, pp. 2154-2159.

Mizote, Isamu et al., "Distal protection improved reperfusion and reduced left ventricular dysfunction in patients with acute myocardial infarction who had angioscopically defined ruptured plaque," Circulation, (Aug. 16, 2005), vol. 112, pp. 1001-1007.

Mizuguchi, H., et al., "Intratumor adminstration of fusogenic liposomes containing fragment A of diphtheria toxin suppresses tumor growth," Cancer Letters, (1996), vol. 100, No. 1-2, pp. 63-69.

Montalescot, Gilles et al., "Platelet glycoprotein IIb/IIIa inhibition with coronary stenting for acute myocardial infarction," N Engl J Med, (Jun. 21, 2001), vol. 344, No. 25, pp. 1895-1903.

Morishima, Itsuro et al., "Angiographic no-reflow phenomenon as a predictor of adverse long-term outcome in patients treated with percutaneous transluminal coronary angioplasty for first acute myocardial infarction," J Am Coll Cardiol, (Oct. 2000), vol. 36, No. 4 pp. 1202-1209.

Ndrepepa, Gjin et al., "5-year prognostic value of no-reflow phenomenon after percutaneous coronary intervention in patients with acute myocardial infarction," J Am Coll Cardiology, (May 25, 2010), vol. 55, No. 21, pp. 2383-2389.

Non-Final Office Action received in U.S. Appl. No. 13/808,027 dated Jul. 12, 2013 (20 pages).

Notice of Allowance received for U.S. Appl. No. 13/808,027 dated Jan. 25, 2016, 10 pages.

Office Action received for Japanese Patent Application No. 2013-518868 dated Jun. 27, 2015, 10 pages with English translation.

Okamura, Atsunori et al., "Detection of embolic particles with the Doppler guide wire during coronary intervention in patients with acute myocardial infarction: efficacy of distal protection device," J Am Coll Cardiol, (Jan. 18, 2005), vol. 45, No. 2, pp. 212-215.

Pasceri, Vincenzo et al., "Effects of the Nitric Oxide Donor Nitroprusside on No-Reflow Phenomenon During Coronary Interventions for Acute Myocardial Infarction," Am J Cardiol, (Jun. 1, 2005), vol. 95, Issue 11, pp. 1358-1361.

Reddy, K. Rajender, "Controlled-Release, Pegylation, Liposomal Formulations: New Mechanisms in the Delivery of Injectable Drugs," Ann Pharmacother., (Jul./Aug. 2000), vol. 34, pp. 915-923.

Reffelmann, Thorsten et al., "No-reflow phenomenon persists long-term after ischemia/reperfusion in the rat and predicts infarct expansion," Circulation, (Dec. 9, 2003), vol. 108, pp. 2911-2917.

Rezkalla, Shereif H. et al., "No-Reflow Phenomenon," Circulation, (Feb. 5, 2002), 105, pp. 656-662.

Ross, Allan M. et al., "A Randomized, Double-Blinded, Placebo-Controlled Multicenter Trial of Adenosine as an Adjunct to Reperfusion in the Treatment of Acute Myocardial Infarction (AMISTAD-II)," J Am Coll Cardiol, (Jun. 7, 2005), vol. 45, No. 11, pp. 1775-1780.

Schiller, Peter W. et al., "Synthesis and in vitro opioid activity profiles of DALDA analogues," Eur J Med Chem, (Oct. 2000), vol. 35, Issue 10, pp. 895-901.

Second Office Action received in Chinese Patent Application No. 201180042936.5 dated Nov. 5, 2014, 9 pages with English translation.

Simes, R.J. et al., "Link Between the Angiographic Substudy and Mortality Outcomes in a Large Randomized Trial of Myocardial Reperfusion: Importance of Early and Complete Infarct Artery Reperfusion," Circulation, (Apr. 1, 1995), vol. 91, No. 7, pp. 1923-1928.

Staat, Patrick et al., "Postconditioning the Human Heart," Circulation, (Oct. 4, 2005), vol. 112, pp. 2143-2148.

Stone, Gregg W. et al., "Distal Microcirculatory Protection During Percutaneous Coronary Intervention in Acute ST-Segment Elevation Myocardial Infarction: A Randomized Controlled Trial," JAMA, (Mar. 2, 2005), vol. 293, No. 9, pp. 1063-1072.

Summers, William K. et al., "The No Reflow Phenomenon in Renal Ischemia," Lab Invest., (Dec. 1971), vol. 25, No. 6, pp. 635-643.

Szeto, Hazel H., "Mitochondria-Targeted Cytoprotective Peptides for Ischemia-Reperfusion Injury," Antioxid. Redox Signal, (2008), vol. 10, No. 3, pp. 601-619.

Tanaka, Atsushi et al., "No-Reflow Phenomenon and Lesion Morphology in Patients With Acute Myocardial Infarction," Circulation, (May 7, 2002), vol. 105, pp. 2148-2152.

Taniyama, Yoshiaki et al., "Beneficial Effect of Intracoronary Verapamil on Microvascular and Myocardial Salvage in Patients With Acute Myocardial Infarction," J Am Coll Cardiol, (Nov. 1, 1997), vol. 30, No. 5, pp. 1193-1199.

Taylor, Andrew J. et al., "Detection of Acutely Impaired Microvascular Reperfusion After Infarct Angioplasty With Magnetic Resonance Imaging ," Circulation, (May 4, 2004), vol. 109, pp. 2080-2085.

Théroux, P. et al., "Inhibition of the Sodium-Hydrogen Exchanger With Cariporide to Prevent Myocardial Infarction in High-Risk Ischemic Situations: Main Results of the GUARDIAN Trial", Circulation, (Dec. 19/26, 2000), vol. 102, pp. 3032-3038.

Théroux, Pierre, "Myocardial Cell Protection: A Challenging Time for Action and a Challenging Time for Clinical Research," Circulation, (Jun. 27, 2000), vol. 101, pp. 2874-2876.

Third Office Action received for Chinese Patent Application No. 201180042936.5 dated Jul. 28, 2015, 9 pages with English translation.

Topol, Eric J. et al., "Recognition of the Importance of Embolization in Atherosclerotic Vascular Disease," Circulation, (Feb. 8, 2000), vol. 101, pp. 570-580.

Tsang, Andrew et al., "Postconditioning: A Form of "Modified Reperfusion" Protects the Myocardium by Activating the Phosphatidylinositol 3-Kinase-Akt Pathway," Circ Res, (2004), vol. 95, pp. 230-232.

Umemura, Shigeo et al., "The effect of verapamil on the restoration of myocardial perfusion and functional recovery in patients with angiographic no-reflow after primary percutaneous coronary intervention," Nucl Med Commun, (Mar. 2006), vol. 27, No. 3, pp. 247-254.

Villanueva, F.S. et al., "Characterization of spatial patterns of flow within the reperfused myocardium by myocardial contrast echocardiography. Implications in determining extent of myocardial salvage," Circulation, (Dec. 1993), vol. 88, No. 6, pp. 2596-2606.

Wehrens, Xander H.T. et al., "A comparison of electrocardiographic changes during reperfusion of acute myocardial infarction by thrombolysis or percutaneous transluminal coronary angioplasty," Am Heart J, (Mar. 2000), vol. 139, No. 3, pp. 430-436.

Weiner, Alan L., "Liposomes for Protein Delivery: Selecting Manufacture and Development Processes," Immunomethods, (1994), 4(3), pp. 201-209.

Wu, Katherine C. et al., "Prognostic Significance of Microvascular Obstruction by Magnetic Resonance Imaging in Patients With Acute Myocardial Infarction," Circulation, (1998), vol. 97, pp. 765-772.

Yamamoto, Koichi et al., "Two different coronary blood flow velocity patterns in thrombolysis in myocardial infarction flow grade 2 in acute myocardial infarction: insight into mechanisms of microvascular dysfunction," J Am Coll Cardiol, (2002), vol. 40, No. 10, pp. 1755-1760.

Yano, Akio et al., "Myocardial Contrast Echocardiography With a New Calibration Method Can Estimate Myocardial Viability in Patients With Myocardial Infarction," J Am Coll Cardiol, (May 19, 2004), vol. 43, No. 10, pp. 1799-1806.

Zeymer, Uwe et al., "The Na(+)/H(+) exchange inhibitor eniporide as an adjunct to early reperfusion therapy for acute myocardial infarction. Results of the evaluation of the safety and cardioprotective effects of eniporide in acute myocardial infarction (ESCAMI) trial," J Am Coll Cardiol, (Nov. 15, 2001), vol. 38, No. 6, pp. 1644-1650.

Zhao, Guo-Min et al., "Comparison of [Dmt1]DALDA and DAMGO in Binding and G Protein Activation at µ, δ, and κ Opioid Receptors," J. Pharmacol Exp Ther., (2003), vol. 307, No. 3, pp. 947-954.

(56) References Cited

OTHER PUBLICATIONS

Zhao, Kesheng et al., Transcellular Transport of a Highly Polar 3+ Net Charge Opioid Tetrapeptide, J. Pharmacol Exp Ther., (2003), vol. 304, No. 1, pp. 425-432.

Zhao, Kesheng et. al., "Cell-permeable Peptide Antioxidants Targeted to Inner Mitochondrial Membrane inhibit Mitochondrial Swelling, Oxidative Cell Death, and Reperfusion Injury," J Biol Chem., (Aug. 2004), vol. 279, No. 33, pp. 34682-34690.

Zijlstra, Felix et al., "A Comparison of Immediate Coronary Angioplasty with Intravenous Streptokinase in Acute Myocardial Infarction," N Engl J Med, (Mar. 11, 1993), vol. 328, No. 10, pp. 680-684.

Office Action issued on Canadian Application 2,804,404, dated Jun. 6, 2017.

Office Action issued on Japanese Application 2013-518868, dated May 15, 2017, English translation.

Cardiac Practice, "Oxidative Stress and Cardiomyocyte Injury," vol. 18, No. 4, 2007 English translation not available.

Kloner et al., "The effect of streptokinase on intramyocardial hemorrhage, infarct size, and the no-reflow phenomenon during coronary reperfusion," Circulation, vol. 70, No. 3, Sep. 1984, pp. 513-521.

Office Action issued on Japanese Application 2016-136149, dated Dec. 11, 2017, English translation only.

\* cited by examiner

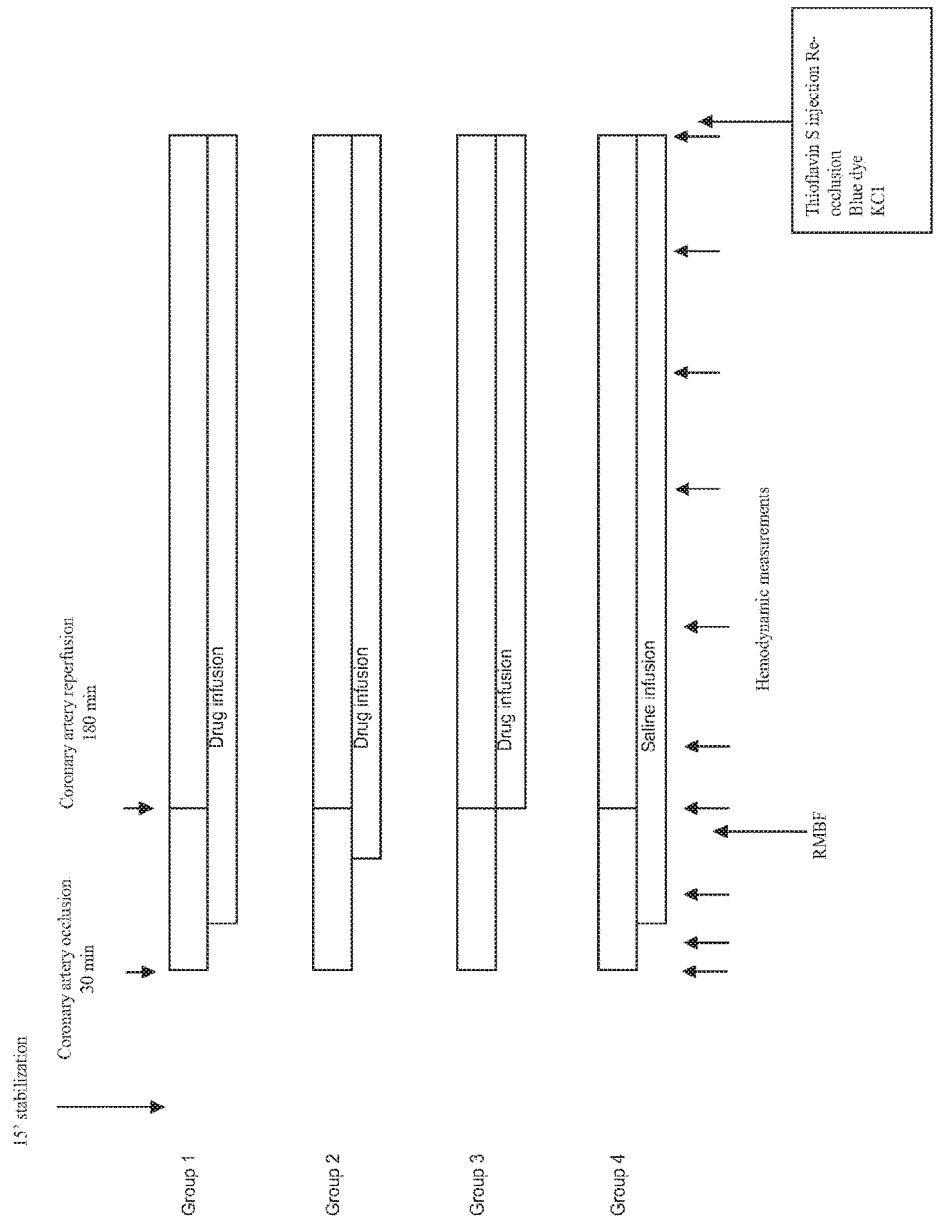

FIG. 2A

| Study Flow Chart - *In-Vivo* Procedures ||||||||
|---|---|---|---|---|---|---|---|
| Rabbit # | | Body Wt (kg) | | | Date | | Group |
| | | | | | | | |
| Dose = | | Dose | | | Infusion Rate | | |
| Clock time | Protocol time | | | | Event | | |
| | | | | | End surgery | | |
| | -15 | | | | Randomize to treatment group | | |
| | -1 | | | | Hemo | | |
| | 0 | occlude | | | | | |
| | 5' occl | | | | Hemo | | |
| | 10' occl | | | | | | Dose if Group 1 vs 4 |
| | 15' occl | | | | Hemo | | |
| | 20' occl | | | | | | Treat if Group 5 |
| | 25' occl | | RMBF | | | | |
| | 29' occl | | | | Hemo | | |
| | 30' occl | reperfuse | | | | | Treat if Group 5 |
| | 5' rep | | | | | | |
| | 30' rep | | | | Hemo | | |
| | 60' rep | | | | Hemo | | |
| | 90' rep | | | | Hemo | | |
| | 120' rep | | | | Hemo | | |
| | 150' rep | | | | Hemo | | |
| | 180' rep | | | | Hemo | | End infusion all groups |
| | End | | Thioflavin S | | | | |
| | | Monastryl Blue pigment | | | | | |
| | | Remove heart | | | | | |

FIG. 2B

| Study Flow Chart - Pathologic Measurements ||||||| 
|---|---|---|---|---|---|---|
| Heart wt (g) | | | RMBF | | | |
| Apex | | | Sample | Region | Weight (g) | |
| 2 | | | 1 | Ischemic | 0. | |
| 3 | | | 2 | Ischemic | 0. | |
| 4 | | | 3 | Normal | 0. | |
| 5 | | | 4 | Normal | 0. | |
| 6 | | | | | | |
| 7 | | | Group 1 | Start D-Arg-2',6'-Dmt-Lys-Phe-NH2 (acetate salt) infusion @ 10' post occlusion || |
| 8 | | | Group 2 | Start D-Arg-2',6'-Dmt-Lys-Phe-NH2 (acetate salt) infusion @ 20' post occlusion || |
| | | | Group 3 | Start D-Arg-2',6'-Dmt-Lys-Phe-NH2 (acetate salt) immediately prior to reperfusion || |
| | | | Group 4 | Start vehicle infusion @ 10' post occlusion || |

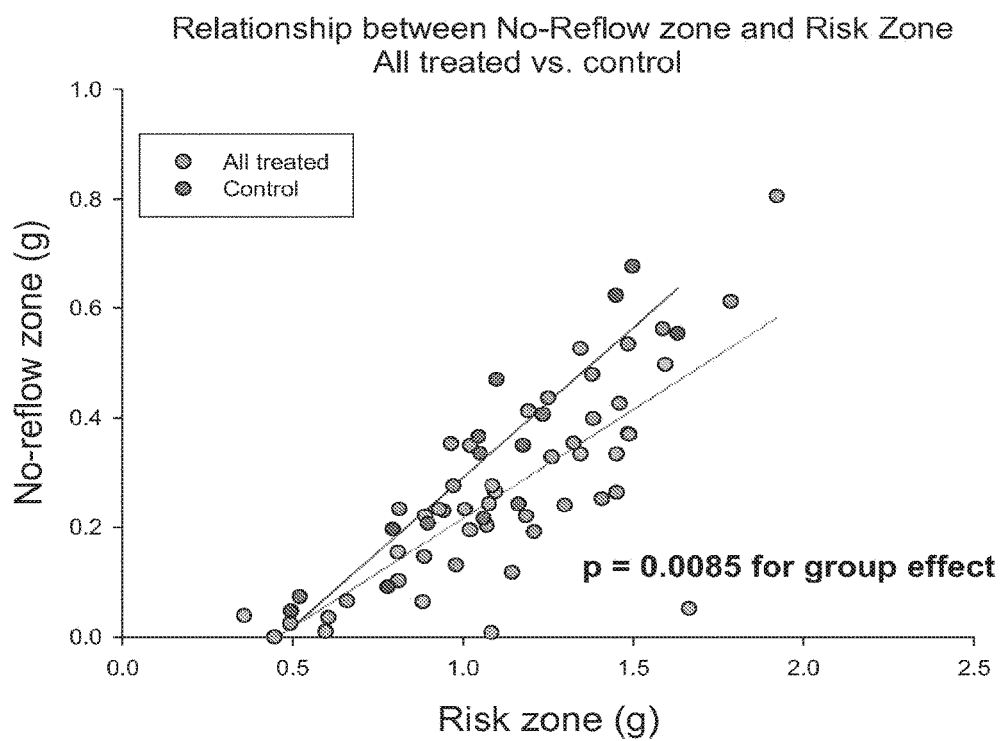

All treated (n=21) vs. control (n=8) with smaller risk zones

AR greater than 10%, but less than mean for all animals (31% of LV)

All treated (n=28) vs. control (n=7) with larger risk zones

AR greater than 31% of LV

METHODS FOR THE PREVENTION OR TREATMENT OF NO-REFLOW FOLLOWING ISCHEMIA/REPERFUSION INJURY

CROSS REFERENCE TO RELATED APPLICATIONS

The present application is a continuation of U.S. application Ser. No. 13/808,027, filed Apr. 12, 2013, which is the U.S. National Stage of PCT/US2011/043424 filed on Jul. 8, 2011, which claims priority to and the benefit of U.S. Provisional Patent Application Ser. No. 61/363,129, filed Jul. 9, 2010; 61/363,133, filed Jul. 9, 2010; and 61/412,655 filed Nov. 11, 2010, the entire disclosures of which are incorporated herein by reference in their entireties.

TECHNICAL FIELD

The present technology relates generally to compositions and methods of preventing or treating ischemia/reperfusion tissue injury. In particular, embodiments of the present technology relate to administering aromatic-cationic peptides in effective amounts to prevent or treat an anatomic zone of no re-flow in mammalian subjects, at risk for, or suffering from, ischemia/reperfusion tissue injury.

BACKGROUND

The following description is provided to assist the understanding of the reader. None of the information provided or references cited is admitted to be prior art.

After acute myocardial infarction (AMI), the immediate therapeutic goal is to establish patency of the infarct-related artery. The successful restoration of epicardial coronary artery patency, however, does not necessarily translate into improved tissue perfusion. Structural disruption or obstruction of the microvasculature, the so-called "no-reflow" phenomenon, could occur before or because of percutaneous coronary intervention (PCI) and can impair coronary flow. Patients with the no re-flow phenomenon have a poor clinical prognosis. The no re-flow phenomenon is generally associated with the presence of an anatomic zone of no re-flow in the tissue. Advances in imaging modalities have improved visualization of no re-flow, showing its frequency to be higher than was estimated by clinical judgment alone. This phenomenon is important because it correlates with infarct size and provides useful prognostic information. No re-flow is associated with reduced left ventricular ejection fraction, left ventricular remodeling, and poor clinical outcomes, placing patients with this effect in a high-risk group among reperfused patients. Attention has shifted, therefore, away from merely achieving epicardial artery patency and towards the status of the microvasculature which can lead to anatomic zones of no re-flow.

SUMMARY

The present technology relates to the treatment or prevention of cardiac ischemia-reperfusion injury in mammals through administration of therapeutically effective amounts of aromatic-cationic peptides, such as D-Arg-2',6'-Dmt-Lys-Phe-NH$_2$, or pharmaceutically acceptable salts thereof, such as acetate salt or trifluoroacetate salt, to subjects in need thereof. In some embodiments, the present technology relates to method useful in the treatment or prevention of an anatomic zone of no-reflow, zone of hemorrhage and infarct size following ischemia/reperfusion.

In some aspects, the disclosure provides a method of treating or preventing an anatomic zone of no re-flow, comprising administering to a subject in need thereof a therapeutically effective amount of an aromatic-cationic peptide or a pharmaceutically acceptable salt thereof, e.g, D-Arg-2',6'-Dmt-Lys-Phe-NH$_2$, or pharmaceutically acceptable salts thereof, such as acetate salt or trifluoroacetate salt. In some embodiments, the method further comprises performing a revascularization procedure on the subject. In some embodiments, the aromatic-cationic peptide is a peptide having:
 at least one net positive charge;
 a minimum of four amino acids;
 a maximum of about twenty amino acids;
 a relationship between the minimum number of net positive charges ($p_m$) and the total number of amino acid residues (r) wherein $3p_m$ is the largest number that is less than or equal to r+1; and a relationship between the minimum number of aromatic groups (a) and the total number of net positive charges ($p_t$) wherein $2a$ is the largest number that is less than or equal to $P_t$+1, except that when a is 1, $P_t$ may also be 1. In particular embodiments, the subject is a human.

In some embodiments, $2p_m$ is the largest number that is less than or equal to r+1, and a may be equal to $p_t$. The aromatic-cationic peptide may be a water-soluble peptide having a minimum of two or a minimum of three positive charges. In some embodiments, the peptide comprises one or more non-naturally occurring amino acids, for example, one or more D-amino acids. In some embodiments, the C-terminal carboxyl group of the amino acid at the C-terminus is amidated. In certain embodiments, the peptide has a minimum of four amino acids. The peptide may have a maximum of about 6, a maximum of about 9, or a maximum of about 12 amino acids.

In some embodiments, the peptide comprises a tyrosine or a 2',6'-dimethyltyrosine (Dmt) residue at the N-terminus. For example, the peptide may have the formula Tyr-D-Arg-Phe-Lys-NH$_2$ or 2',6'-Dmt-D-Arg-Phe-Lys-NH$_2$. In another embodiment, the peptide comprises a phenylalanine or a 2',6'-dimethylphenylalanine residue at the N-terminus. For example, the peptide may have the formula Phe-D-Arg-Phe-Lys-NH$_2$ or 2',6'-Dmp-D-Arg-Phe-Lys-NH$_2$. In a particular embodiment, the aromatic-cationic peptide has the formula D-Arg-2',6'-Dmt-Lys-Phe-NH$_2$ or a pharmaceutically acceptable salt thereof such as acetate salt or trifluoroacetate salt.

In one embodiment, the peptide is defined by formula I:

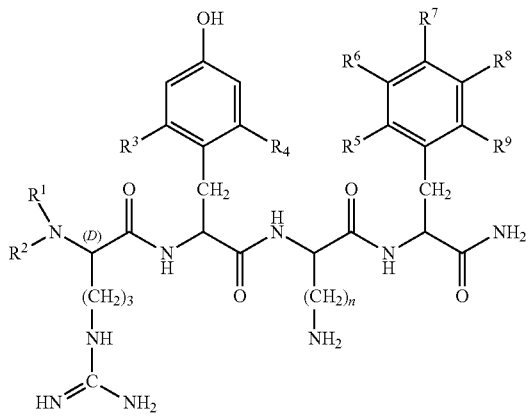

wherein $R^1$ and $R^2$ are each independently selected from
(i) hydrogen;
(ii) linear or branched $C_1$-$C_6$ alkyl;

(iii) 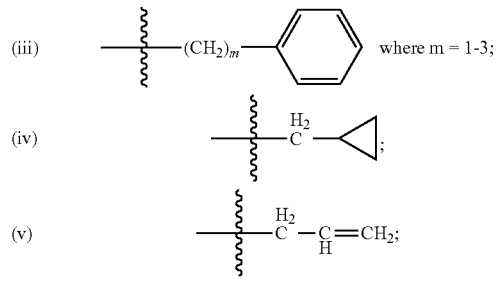 where m = 1-3;

(iv)

(v)

$R^3$ and $R^4$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo;
$R^5$, $R^6$, $R^7$, $R^8$, and $R^9$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo; and
n is an integer from 1 to 5.

In a particular embodiment, $R^1$ and $R^2$ are hydrogen; $R^3$ and $R^4$ are methyl; $R^5$, $R^6$, $R^7$, $R^8$, and $R^9$ are all hydrogen; and n is 4.

In one embodiment, the peptide is defined by formula II:

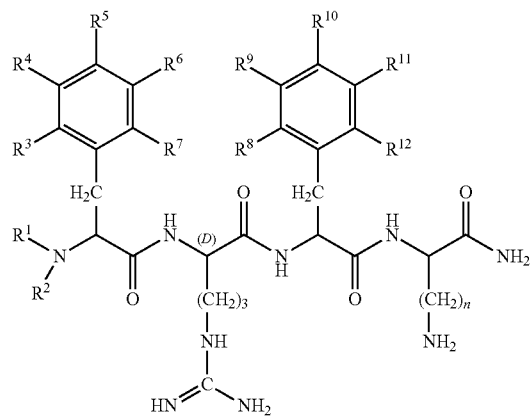

wherein $R^1$ and $R^2$ are each independently selected from
(i) hydrogen;
(ii) linear or branched $C_1$-$C_6$ alkyl;

(iii) 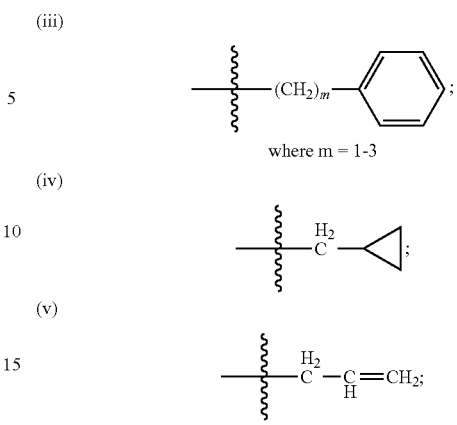

where m = 1-3

(iv)

(v)

$R^3$, $R^4$, $R^5$, $R^6$, $R^7$, $R^8$, $R^9$, $R^{10}$, $R^{11}$ and $R^{12}$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo; and
n is an integer from 1 to 5.

In a particular embodiment, $R^1$, $R^2$, $R^3$, $R^4$, $R^5$, $R^6$, $R^7$, $R^8$, $R^9$, $R^{10}$, $R^{11}$, and $R^{12}$ are all hydrogen; and n is 4. In another embodiment, $R^1$, $R^2$, $R^3$, $R^4$, $R^5$, $R^6$, $R^7$, $R^8$, $R^9$, and $R^{11}$ are all hydrogen; $R^8$ and $R^{12}$ are methyl; $R^{10}$ is hydroxyl; and n is 4.

The aromatic-cationic peptides may be administered in a variety of ways. In some embodiments, the peptides may be administered orally, topically, intranasally, intraperitoneally, intravenously, subcutaneously, or transdermally (e.g., by iontophoresis). In some embodiments, the aromatic-cationic peptide is administered by an intracoronary route or an intra-arterial route.

In one embodiment, the present technology provides a method for preventing or treating anatomic zone of no re-flow in a mammalian subject in need thereof, the method comprising administering to the subject a therapeutically effective amount of a peptide D-Arg-2',6'-Dmt-Lys-Phe-NH$_2$ or a pharmaceutically acceptable salt thereof, such as acetate salt or trifluoroacetate salt, thereby preventing or treating microvasular injury in the subject. In one embodiment, the method further comprises the step of performing a revascularization procedure on the subject. In one embodiment, the anatomic zone of no re-flow is a disruption or obstruction of the microvasculature of the subject. In one embodiment, the mammalian subject is at risk for, or suffering from an anatomic zone of no re-flow. In one embodiment, the subject is at risk for, or suffering from, an anatomic zone of no re-flow associated with cardiovascular tissue, or in cardiovascular tissue. In one embodiment, the subject is at risk for, or suffering from, an anatomic zone of no re-flow associated with cerebral tissue, or in cerebral tissue. In one embodiment, the subject is at risk for, or suffering from, an anatomic zone of no re-flow associated with renal tissue, or in renal tissue. In one embodiment, the subject is at risk for, or suffering from, an anatomic zone of no re-flow associated with skeletal tissue, or in skeletal tissue. In one embodiment, the anatomic zone of no re-flow has a disruption or obstruction of the microvasculature of the subject. In one embodiment, the subject is administered the peptide prior to formation of the anatomic zone of no re-flow. In one embodiment, the subject is administered the peptide after the formation of the anatomic zone no re-flow.

In one embodiment, the subject is administered the peptide prior to the revascularization procedure. In another embodiment, the subject is administered the peptide after the revascularization procedure. In another embodiment, the subject is administered the peptide during and after the revascularization procedure. In yet another embodiment, the subject is administered the peptide continuously before, during, and after the revascularization procedure.

In one embodiment, the subject is administered the peptide for at least 3 hours, at least 5 hours, at least 8 hours, at least 12 hours, or at least 24 hours after the revascularization procedure. In one embodiment, the subject is administered the peptide starting at least 8 hours, at least 4 hours, at least 2 hours, at least 1 hour, or at least 10 minutes prior to the revascularization procedure.

In various embodiments, the subject is suffering from a myocardial infarction, a stroke, or is in need of angioplasty. In one embodiment, the revascularization procedure is selected from the group consisting of: balloon angioplasty; insertion of a bypass graft; insertion of a stent; percutaneous transluminal coronary angioplasty; or directional coronary atherectomy. In one embodiment, the revascularization procedure is removal of an occlusion. In one embodiment, the revascularization procedure is administration of one or more thrombolytic agents. In one embodiment, the one or more thrombolytic agents are selected from the group consisting of: tissue plasminogen activator, urokinase; prourokinase; streptokinase; acylated form of plasminogen; acylated form of plasmin; and acylated streptokinase-plasminogen complex.

In some embodiments, the vessel occlusion is selected from the group consisting of: deep venous thrombosis; peripheral thrombosis; embolic thrombosis; hepatic vein thrombosis; sinus thrombosis; venous thrombosis; an occluded arterio-venal shunt; and an occluded catheter device.

In one aspect, the present disclosure provides a method of coronary revascularization comprising: (a) administering to a mammalian subject a therapeutically effective amount of the peptide D-Arg-2',6'-Dmt-Lys-Phe-NH$_2$ or a pharmaceutically acceptable salt thereof such as acetate salt or trifluoroacetate salt; and (b) performing a coronary artery bypass graft procedure on the subject.

BRIEF DESCRIPTION OF THE FIGURES

FIG. 1 is an illustration of the study design for animals used in the examples.

FIGS. 2A and 2B are study flow charts illustrative of in vivo study procedure and pathologic measurements, respectively.

FIG. 8 is a graph showing the relationship between the risk zone and the no-reflow zone in the treated and control groups in a rabbit model of AMI.

DETAILED DESCRIPTION

Figure 3:
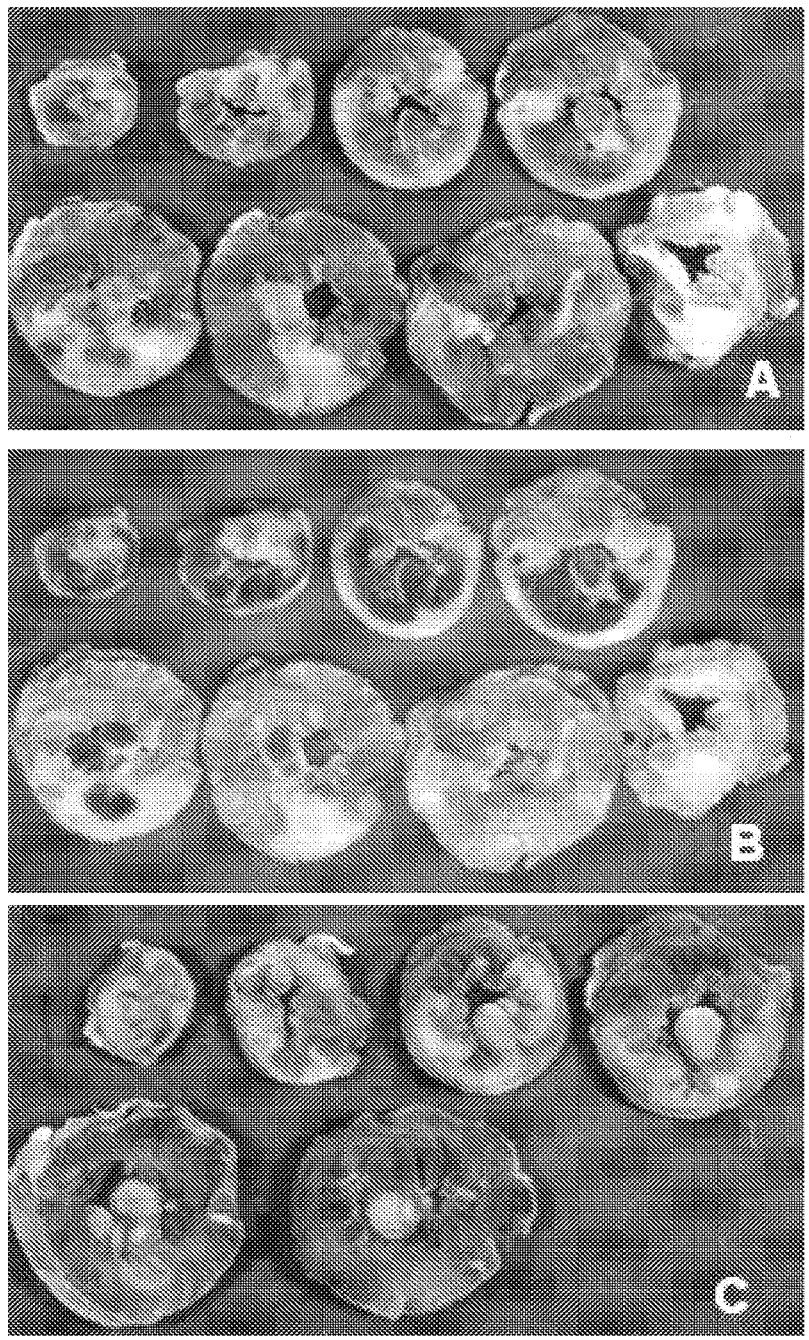
FIG. 3 illustrates the use of histological staining technique to assess heart tissue from a control rabbit subjected to heart ischemia/reperfusion using the model described in Example 1. Panels A through C show exemplary heart slices from one representative control rabbit. Panel A: Photograph showing the ischemic risk area. The coronary artery is re-occluded at the end of the reperfusion period and Unisperse blue is injected through the left atrial catheter. Blue areas are perfused zones within the heart, and areas lacking blue dye are not perfused. Panel B: No-reflow zone (thioflavin S staining as photographed under ultraviolet light). Thioflavin S is injected through the left atrial catheter at the end of the reperfusion period before re-occluding the artery. Regions with intact vessels are fluorescent, and areas of no-reflow appear dark. Panel C: Heart slices after incubation in TTC. Regions of necrotic tissue appear white, and non-necrotic tissue stains red.

It is to be appreciated that certain aspects, modes, embodiments, variations and features of the invention are described below in various levels of detail in order to provide a substantial understanding of the present invention.

In practicing the present invention, many conventional techniques in molecular biology, protein biochemistry, cell biology, immunology, microbiology and recombinant DNA are used. These techniques are well-known and are explained in, e.g., *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N.Y., 1989); *DNA Cloning: A Practical Approach*, Vols. I and II, Glover, Ed. (1985); *Oligonucleotide Synthesis*, Gait, Ed. (1984); Nucleic Acid llybridization, Hames & Higgins, Eds. (1985); *Transcription and Translation*, Hames & Higgins, Eds. (1984); *Animal Cell Culture*, Freshney, Ed. (1986); *Immobilized Cells and Enzymes* (IRL Press, 1986); Perbal, *A Practical Guide to Molecular Cloning*; the series, *Meth. Enzymol.*, (Academic Press, Inc., 1984); *Gene Transfer Vectors for Mammalian Cells*, Miller & Calos, Eds. (Cold Spring Harbor Laboratory, N Y, 1987); and *Meth. Enzymol.*, Vols. 154 and 155, Wu & Grossman, and Wu, Eds., respectively.

The definitions of certain terms as used in this specification are provided below. Unless defined otherwise, all technical and scientific terms used herein generally have the same meaning as commonly understood by one of ordinary skill in the art to which this invention belongs.

As used in this specification and the appended claims, the singular forms "a", "an" and "the" include plural referents unless the content clearly dictates otherwise. For example, reference to "a cell" includes a combination of two or more cells, and the like.

As used herein, the "administration" of an agent, drug, or peptide to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. In some embodiments, the aromatic-cationic peptide is administered by an intracoronary route or an intra-arterial route. Administration includes self-administration and the administration by another.

As used herein, the term "amino acid" includes naturally-occurring amino acids and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics refers to chemical compounds that have a structure that is different from the general chemical structure of an amino acid, but that functions in a manner similar to a naturally-occurring amino acid. Amino acids can be referred to herein by either their commonly known three letter symbols or by the one-letter symbols recommended by the IUPAC-IUB Biochemical Nomenclature Commission.

As used herein, the term "effective amount" refers to a quantity sufficient to achieve a desired therapeutic and/or prophylactic effect, e.g., an amount which results in the prevention of, or a decrease in, cardiac ischemia-reperfusion injury or one or more symptoms associated with cardiac ischemia-reperfusion injury. In the context of therapeutic or prophylactic applications, the amount of a composition administered to the subject will depend on the type and severity of the disease and on the characteristics of the individual, such as general health, age, sex, body weight and tolerance to drugs. It will also depend on the degree, severity and type of disease. The skilled artisan were able to determine appropriate dosages depending on these and other factors. The compositions can also be administered in combination with one or more additional therapeutic compounds. In the methods described herein, the aromatic-cationic peptides may be administered to a subject having one or more signs or symptoms of a zone of no-reflow. In other embodiments, the mammal has one or more signs or symptoms of myocardial infarction, such as chest pain described as a pressure sensation, fullness, or squeezing in the mid portion of the thorax; radiation of chest pain into the jaw or teeth, shoulder, arm, and/or back; dyspnea or shortness of breath; epigastric discomfort with or without nausea and vomiting; and diaphoresis or sweating. For example, a "therapeutically effective amount" of the aromatic-cationic peptides is meant levels in which the physiological effects of anatomic zone of no re-flow injury are, at a minimum, ameliorated.

As used herein the term "ischemia reperfusion injury" refers to the damage caused first by restriction of the blood supply to a tissue followed by a sudden resupply of blood and the attendant generation of free radicals. Ischemia is a decrease in the blood supply to the tissue and is followed by reperfusion, a sudden perfusion of oxygen into the deprived tissue.

An "isolated" or "purified" polypeptide or peptide is substantially free of cellular material or other contaminating polypeptides from the cell or tissue source from which the agent is derived, or substantially free from chemical precursors or other chemicals when chemically synthesized. For example, an isolated aromatic-cationic peptide would be free of materials that would interfere with diagnostic or therapeutic uses of the agent. Such interfering materials may include enzymes, hormones and other proteinaceous and nonproteinaceous solutes.

As used herein, the terms "polypeptide", "peptide", and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art.

As used herein, the terms "treating" or "treatment" or "alleviation" refers to both therapeutic treatment and prophylactic or preventative measures, wherein the object is to prevent or slow down (lessen) the targeted pathologic condition or disorder. A subject is successfully "treated" for no-reflow injury if, after receiving a therapeutic amount of the aromatic-cationic peptides according to the methods described herein, the subject shows observable and/or measurable reduction in the size of an anatomic zone of no-reflow. It is also to be appreciated that the various modes of treatment or prevention of medical conditions as described are intended to mean "substantial", which includes total but also less than total treatment or prevention, and wherein some biologically or medically relevant result is achieved.

As used herein, "prevention" or "preventing" of a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. As used herein, preventing ischemia-reperfusion injury includes preventing oxidative damage or preventing mitochondrial permeability transitioning, thereby preventing or ameliorating the harmful effects of the loss and subsequent restoration of blood flow to the heart.

Methods of Prevention or Treatment of No-Reflow Injury

The rapid restoration of coronary flow to the jeopardized myocardium is an important part of therapy after acute myocardial infarction. Despite an open infarct-related artery, breakdown of or obstruction to coronary microvasculature can markedly reduce blood flow to the infarct zone, leading to the formation of an anatomic zone of no re-flow. This effect is known as the no-reflow phenomenon. The no-reflow phenomenon occurs in a notable proportion of patients with AMI, despite aggressive reperfusion therapy, and is associated with a poor prognosis. Ito, H., No-reflow phenomenon and prognosis in patients with acute myocardial infarction, *Nature Clinical Practice Cardiovascular Medicine* (2006) 3, 499-506. Moreover, the extent of no-reflow is a good predictor of AMI patient outcomes. After infarction, microvascular obstruction predicts more frequent cardiovascular complications and relates directly to long-term prognosis in patients with AMI (infarct expansion, hospitalization, mortality, major adverse cardiac events, etc.). Wu et al., Prognostic significance of microvascular obstruction by magnetic resonance imaging in patients with acute myocardial infarction. *Circulation* 1998, 97: 765-772; Ndrepapa et al. 5-year prognostic value of no-reflow phenomenon after percutaneous coronary intervention in patients with acute myocardial infarction. *J Am Coll Cardiology* 2010, 55(21): 2383-2389; Bolognese et al. Impact of microvascular dysfunction on left ventricular remodeling and long-term clinical outcome after primary coronary angioplasty for acute myocardial infarction. *Circulation* 2004, 109: 1121-1126;

and Reffelmann et al. No-reflow phenomenon persists long-term after ischemia/reperfusion in the rat and predicts infarct expansion. *Circulation* 2003, 108: 2911-2917.

The no-reflow phenomenon can occur in other organs besides the heart, such as liver, kidney, brain, skin, etc. The no-reflow concept was first suggested in brain ischemia. Brains of rabbits that suffered a brief 2½ minutes of ischemia had normal blood flow when the ischemia was relieved. When the rabbits were exposed to longer ischemic periods, normal flow to brain tissues was not restored, even after relief of the vessel obstruction. Prolonged ischemia resulted in significant changes in the microvasculature that interfered with normal flow to the brain cells. The existence of this phenomenon was confirmed in a variety of animal models of brain ischemia. It was also shown in a variety of other organs, including skin, skeletal muscle, and the kidney. Moreover, microcirculation alterations can modulate the organ damage induced by ischemia-reperfusion injury during organ transplantation. See Majno et al. No-reflow after cerebral ischaemia. *Lancet.* 1967; 2: 569-570; Ames et al. Cerebral ischemia, II: the no-reflow phenomenon. *Am J Pathol.* 1968; 52: 437-447; Cerisoli et al. Experimental cerebral "no-reflow phenomenon": response to intracarotid injection of dexamethasone, furosemide and escina. *J Neurosurg Sci.* 1981; 25: 7-12; Ito et al. Transient appearance of "no-reflow" phenomenon in Mongolian gerbils. *Stroke.* 1980; 11: 517-521; Asano T, Sano K. Pathogenetic role of no-reflow phenomenon in experimental subarachnoid hemorrhage in dogs. *J Neurosurg.* 1977; 46: 454-466; Chait et al. The effects of the perfusion of various solutions on the no-reflow phenomenon in experimental free flaps. *Plast Reconstr Surg.* 1978; 61: 421-430; Allen et al. Pathophysiology and related studies of the no-reflow phenomenon in skeletal muscle. *Clin Orthop.* 1995; 314: 122-133; Summers W K, Jamison R L. The no-reflow phenomenon in renal ischemia. *Lab Invest.* 1971; 25: 635-643; Johnston W H, Latta H. Glomerular mesangial and endothelial cell swelling following temporary renal ischemia and its role in the no-reflow phenomenon. *Am J Pathol.* 1977; 89: 153-166.

The present technology relates to the treatment or prevention of ischemia-reperfusion injury in mammals through administration of therapeutically effective amounts of aromatic-cationic peptides such as D-Arg-2',6'-Dmt-Lys-Phe-NH$_2$, or pharmaceutically acceptable salts thereof, such as acetate salt or trifluoroacetate salt to subjects in need thereof. In one aspect, the present technology relates to method useful in the treatment or prevention of anatomic zone of no-reflow, zone of hemorrhage and infarct size following ischemia/reperfusion. In one embodiment, the treatment of an anatomic zone of no-reflow includes increasing the amount or area of tissue perfusion in a subject compared to a similar subject not administered the aromatic-cationic peptide. In one embodiment, the prevention of an anatomic zone of no-reflow includes reducing the amount or area of microvascular damage caused by reperfusion in a subject compared to a similar subject not administered the aromatic-cationic peptide. In some embodiments, treatment or prevention of an anatomic zone of no-reflow includes reducing injury to the affected vessel upon reperfusion, reducing the effect of plugging by blood cells, and/or reducing endothelial cell swelling in a subject compared to a similar subject not administered the aromatic-cationic peptide. The extent of the prevention or treatment can be measured by any technique known in the art, including but not limited to, MRI in order to assess microvascular damage). Re-flow phenomenon may also be assessed using myocardial contrast echocardiography, coronary angiography, myocardial blush, coronary doppler imaging, electrocardiography, nuclear imaging single-photon emission CT, using thallium or technetium-99m, and PET. Successful prevention or treatment can be determined by comparing the extent of no-reflow in the subject observed by any of these imaging techniques compared to a control subject or a population of control subjects that are not administered the aromatic-cationic peptide.

In one aspect, the present technology relates to the treatment or prevention of an anatomic zone of no re-flow by administration of certain aromatic-cationic peptides, such as D-Arg-2',6'-Dmt-Lys-Phe-NH$_2$, or pharmaceutically acceptable salts thereof, such as acetate salt or trifluoroacetate salt, to a subject in need thereof. In one embodiment, the administration of the aromatic-cationic peptide(s) to a subject is before the formation of the anatomic zone of no re-flow. In another embodiment, the administration of the aromatic-cationic peptide(s) to a subject is after the formation of an anatomic zone of no re-flow. In one embodiment, the method is performed in conjunction with a revascularization procedure. Also provided is a method for the treatment or prevention of cardiac ischemia-reperfusion injury. Also provided is a method of treating a myocardial infarction in a subject to prevent injury to the heart upon reperfusion. In one aspect, the present technology relates to a method of coronary revascularization comprising administering to a mammalian subject a therapeutically effective amount of the aromatic cationic peptide and performing coronary artery bypass graft (CABG) procedure on the subject.

In one embodiment, the subject is administered the peptide such as D-Arg-2',6'-Dmt-Lys-Phe-NH$_2$, or pharmaceutically acceptable salts thereof, such as acetate salt or trifluoroacetate salt, prior to a revascularization procedure. In another embodiment, the subject is administered the peptide after the revascularization procedure. In another embodiment, the subject is administered the peptide during and after the revascularization procedure. In yet another embodiment, the subject is administered the peptide continuously before, during, and after the revascularization procedure. In another embodiment, the subject is administered the peptide regularly (i.e., chronically) following an AMI and/or a revascularization or CABG procedure.

In some embodiments, the subject is administered the peptide after the revascularization procedure. In one embodiment, the subject is administered the peptide for at least 3 hours, at least 5 hours, at least 8 hours, at least 12 hours, or at least 24 hours after the revascularization procedure. In some embodiments, the subject is administered the peptide prior to the revascularization procedure. In one embodiment, the subject is administered the peptide starting at least 8 hours, at least 4 hours, at least 2 hours, at least 1 hour, or at least 10 minutes prior to the revascularization procedure. In one embodiment, the subject is administered for at least one week, at least one month or at least one year after the revascularization procedure. In some embodiments, the subject is administered the peptide prior to and after the revascularization procedure. In some embodiments, the subject is administered the peptide as an infusion over a specified period of time. In some embodiments, the peptide is administered to the subject as a bolus.

The aromatic-cationic peptides are water-soluble and highly polar. Despite these properties, the peptides can readily penetrate cell membranes. The aromatic-cationic peptides typically include a minimum of three amino acids or a minimum of four amino acids, covalently joined by peptide bonds. The maximum number of amino acids present in the aromatic-cationic peptides is about twenty amino acids covalently joined by peptide bonds. Suitably, the maximum number of amino acids is about twelve, more preferably about nine, and most preferably about six.

The amino acids of the aromatic-cationic peptides can be any amino acid. As used herein, the term "amino acid" is used to refer to any organic molecule that contains at least one amino group and at least one carboxyl group. Typically, at least one amino group is at the a position relative to a carboxyl group. The amino acids may be naturally occurring. Naturally occurring amino acids include, for example, the twenty most common levorotatory (L) amino acids normally found in mammalian proteins, i.e., alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan, (Trp), tyrosine (Tyr), and valine (Val). Other naturally occurring amino acids include, for example, amino acids that are synthesized in metabolic processes not associated with protein synthesis. For example, the amino acids ornithine and citrulline are synthesized in mammalian metabolism during the production of urea. Another example of a naturally occurring amino acid includes hydroxyproline (Hyp).

The peptides optionally contain one or more non-naturally occurring amino acids. In some embodiments, the peptide has no amino acids that are naturally occurring. The non-naturally occurring amino acids may be levorotary (L-), dextrorotatory (D-), or mixtures thereof. Non-naturally occurring amino acids are those amino acids that typically are not synthesized in normal metabolic processes in living organisms, and do not naturally occur in proteins. In addition, the non-naturally occurring amino acids suitably are also not recognized by common proteases. The non-naturally occurring amino acid can be present at any position in the peptide. For example, the non-naturally occurring amino acid can be at the N-terminus, the C-terminus, or at any position between the N-terminus and the C-terminus.

The non-natural amino acids may, for example, comprise alkyl, aryl, or alkylaryl groups not found in natural amino acids. Some examples of non-natural alkyl amino acids include β-aminobutyric acid, β-aminobutyric acid, γ-aminobutyric acid, δ-aminovaleric acid, and ε-aminocaproic acid. Some examples of non-natural aryl amino acids include ortho-, meta, and para-aminobenzoic acid. Some examples of non-natural alkylaryl amino acids include ortho-, meta-, and para-aminophenylacetic acid, and γ-phenyl-β-aminobutyric acid. Non-naturally occurring amino acids include derivatives of naturally occurring amino acids. The derivatives of naturally occurring amino acids may, for example, include the addition of one or more chemical groups to the naturally occurring amino acid.

For example, one or more chemical groups can be added to one or more of the 2', 3', 4', 5', or 6' position of the aromatic ring of a phenylalanine or tyrosine residue, or the 4', 5', 6', or 7' position of the benzo ring of a tryptophan residue. The group can be any chemical group that can be added to an aromatic ring. Some examples of such groups include branched or unbranched $C_1$-$C_4$ alkyl, such as methyl, ethyl, n-propyl, isopropyl, butyl, isobutyl, or t-butyl, $C_1$-$C_4$ alkyloxy (i.e., alkoxy), amino, $C_1$-$C_4$ alkylamino and $C_1$-$C_4$ dialkylamino (e.g., methylamino, dimethylamino), nitro, hydroxyl, halo (i.e., fluoro, chloro, bromo, or iodo). Some specific examples of non-naturally occurring derivatives of naturally occurring amino acids include norvaline (Nva) and norleucine (Nle).

Another example of a modification of an amino acid in a peptide is the derivatization of a carboxyl group of an aspartic acid or a glutamic acid residue of the peptide. One example of derivatization is amidation with ammonia or with a primary or secondary amine, e.g. methylamine, ethylamine, dimethylamine or diethylamine. Another example of derivatization includes esterification with, for example, methyl or ethyl alcohol. Another such modification includes derivatization of an amino group of a lysine, arginine, or histidine residue. For example, such amino groups can be acylated. Some suitable acyl groups include, for example, a benzoyl group or an alkanoyl group comprising any of the $C_1$-$C_4$ alkyl groups mentioned above, such as an acetyl or propionyl group.

The non-naturally occurring amino acids are preferably resistant, and more preferably insensitive, to common proteases. Examples of non-naturally occurring amino acids that are resistant or insensitive to proteases include the dextrorotatory (D-) form of any of the above-mentioned naturally occurring L-amino acids, as well as L- and/or D-non-naturally occurring amino acids. The D-amino acids do not normally occur in proteins, although they are found in certain peptide antibiotics that are synthesized by means other than the normal ribosomal protein synthetic machinery of the cell. As used herein, the D-amino acids are considered to be non-naturally occurring amino acids.

In order to minimize protease sensitivity, the peptides should have less than five, preferably less than four, more preferably less than three, and most preferably, less than two contiguous L-amino acids recognized by common proteases, irrespective of whether the amino acids are naturally or non-naturally occurring. In some embodiments, the peptide has only D-amino acids, and no L-amino acids. If the peptide contains protease sensitive sequences of amino acids, at least one of the amino acids is preferably a non-naturally-occurring D-amino acid, thereby conferring protease resistance. An example of a protease sensitive sequence includes two or more contiguous basic amino acids that are readily cleaved by common proteases, such as endopeptidases and trypsin. Examples of basic amino acids include arginine, lysine and histidine.

The aromatic-cationic peptides should have a minimum number of net positive charges at physiological pH in comparison to the total number of amino acid residues in the peptide. The minimum number of net positive charges at physiological pH were referred to below as ($p_m$). The total number of amino acid residues in the peptide were referred to below as (r). The minimum number of net positive charges discussed below are all at physiological pH. The term "physiological pH" as used herein refers to the normal pH in the cells of the tissues and organs of the mammalian body. For instance, the physiological pH of a human is normally approximately 7.4, but normal physiological pH in mammals may be any pH from about 7.0 to about 7.8.

"Net charge" as used herein refers to the balance of the number of positive charges and the number of negative charges carried by the amino acids present in the peptide. In this specification, it is understood that net charges are measured at physiological pH. The naturally occurring amino acids that are positively charged at physiological pH include L-lysine, L-arginine, and L-histidine. The naturally occurring amino acids that are negatively charged at physiological pH include L-aspartic acid and L-glutamic acid.

Typically, a peptide has a positively charged N-terminal amino group and a negatively charged C-terminal carboxyl group. The charges cancel each other out at physiological pH. As an example of calculating net charge, the peptide Tyr-D-Arg-Phe-Lys-Glu-His-Trp-D-Arg has one negatively charged amino acid (i.e., Glu) and four positively charged amino acids (i.e., two Arg residues, one Lys, and one His). Therefore, the above peptide has a net positive charge of three.

In one embodiment, the aromatic-cationic peptides have a relationship between the minimum number of net positive charges at physiological pH ($p_m$) and the total number of amino acid residues (r) wherein $3p_m$ is the largest number that is less than or equal to r+1.

In this embodiment, the relationship between the minimum number of net positive charges ($p_m$) and the total number of amino acid residues (r) is as follows:

TABLE 1

Amino acid number and net positive charges ($3p_m \leq p + 1$)

| (r) | | | | | | | | | | | | | | | | | | |
|---|---|---|---|---|---|---|---|---|---|---|---|---|---|---|---|---|---|---|
| | 3 | 4 | 5 | 6 | 7 | 8 | 9 | 10 | 11 | 12 | 13 | 14 | 15 | 16 | 17 | 18 | 19 | 20 |
| ($p_m$) | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of net positive charges ($p_m$) and the total number of amino acid residues (r) wherein $2p_m$ is the largest number that is less than or equal to r+1. In this embodiment, the relationship between the minimum number of net positive charges ($p_m$) and the total number of amino acid residues (r) is as follows:

TABLE 2

Amino acid number and net positive charges ($2p_m \leq p + 1$)

| (r) | | | | | | | | | | | | | | | | | | |
|---|---|---|---|---|---|---|---|---|---|---|---|---|---|---|---|---|---|---|
| | 3 | 4 | 5 | 6 | 7 | 8 | 9 | 10 | 11 | 12 | 13 | 14 | 15 | 16 | 17 | 18 | 19 | 20 |
| ($p_m$) | 2 | 2 | 3 | 3 | 4 | 4 | 5 | 5 | 6 | 6 | 7 | 7 | 8 | 8 | 9 | 9 | 10 | 10 |

In one embodiment, the minimum number of net positive charges ($p_m$) and the total number of amino acid residues (r) are equal. In another embodiment, the peptides have three or four amino acid residues and a minimum of one net positive charge, suitably, a minimum of two net positive charges and more preferably a minimum of three net positive charges.

It is also important that the aromatic-cationic peptides have a minimum number of aromatic groups in comparison to the total number of net positive charges ($p_t$). The minimum number of aromatic groups were referred to below as (a). Naturally occurring amino acids that have an aromatic group include the amino acids histidine, tryptophan, tyrosine, and phenylalanine. For example, the hexapeptide Lys-Gln-Tyr-D-Arg-Phe-Trp has a net positive charge of two (contributed by the lysine and arginine residues) and three aromatic groups (contributed by tyrosine, phenylalanine and tryptophan residues).

The aromatic-cationic peptides should also have a relationship between the minimum number of aromatic groups (a) and the total number of net positive charges at physiological pH ($p_t$) wherein 3a is the largest number that is less than or equal to $p_t$+1, except that when $p_t$ is 1, a may also be 1. In this embodiment, the relationship between the minimum number of aromatic groups (a) and the total number of net positive charges ($p_t$) is as follows:

TABLE 3

Aromatic groups and net positive charges ($3a \leq p_t + 1$ or $a = p_t = 1$)

| ($p_t$) | | | | | | | | | | | | | | | | | | | |
|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 |
| (a) | 1 | 1 | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of aromatic groups (a) and the total number of net positive charges ($p_t$) wherein 2a is the largest number that is less than or equal to $p_t$+1. In this embodiment, the relationship between the minimum number of aromatic amino acid residues (a) and the total number of net positive charges ($p_t$) is as follows:

TABLE 4

Aromatic groups and net positive charges ($2a \leq p_t + 1$ or $a = p_t = 1$)

| ($p_t$) | | | | | | | | | | | | | | | | | | | |
|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 |
| (a) | 1 | 1 | 2 | 2 | 3 | 3 | 4 | 4 | 5 | 5 | 6 | 6 | 7 | 7 | 8 | 8 | 9 | 9 | 10 | 10 |

In another embodiment, the number of aromatic groups (a) and the total number of net positive charges ($P_t$) are equal.

Carboxyl groups, especially the terminal carboxyl group of a C-terminal amino acid, are suitably amidated with, for example, ammonia to form the C-terminal amide. Alternatively, the terminal carboxyl group of the C-terminal amino acid may be amidated with any primary or secondary amine. The primary or secondary amine may, for example, be an alkyl, especially a branched or unbranched $C_1$-$C_4$ alkyl, or an aryl amine. Accordingly, the amino acid at the C-terminus of the peptide may be converted to an amido, N-methylamido, N-ethylamido, N,N-dimethylamido, N,N-diethylamido, N-methyl-N-ethylamido, N-phenylamido or N-phenyl-N-ethylamido group. The free carboxylate groups of the asparagine, glutamine, aspartic acid, and glutamic acid residues not occurring at the C-terminus of the aromatic-cationic peptides may also be amidated wherever they occur within the peptide. The amidation at these internal positions may be with ammonia or any of the primary or secondary amines described above.

In one embodiment, the aromatic-cationic peptide is a tripeptide having two net positive charges and at least one aromatic amino acid. In a particular embodiment, the aromatic-cationic peptide is a tripeptide having two net positive charges and two aromatic amino acids.

Aromatic-cationic peptides include, but are not limited to, the following peptide examples:

2',6'-Dmp-D-Arg-2',6'-Dmt-Lys-$NH_2$
2',6'-Dmp-D-Arg-Phe-Lys-$NH_2$
2',6'-Dmt-D-Arg-PheOrn-$NH_2$
2',6'-Dmt-D-Arg-Phe-Ahp(2-aminoheptanoicacid)-$NH_2$
2',6'-Dmt-D-Arg-Phe-Lys-$NH_2$
2',6'-Dmt-D-Cit-PheLys-$NH_2$
Ala-D-Phe-D-Arg-Tyr-Lys-D-Trp-His-D-Tyr-Gly-Phe
Arg-D-Leu-D-Tyr-Phe-Lys-Glu-D-Lys-Arg-D-Trp-Lys-D-Phe-Tyr-D-Arg-Gly
Asp-Arg-D-Phe-Cys-Phe-D-Arg-D-Lys-Tyr-Arg-D-Tyr-Trp-D-His-Tyr-D-Phe-Lys-Phe
Asp-D-Trp-Lys-Tyr-D-His-Phe-Arg-D-Gly-Lys-$NH_2$
D-Arg-2',6'-Dmt-Lys-Phe-$NH_2$
D-Glu-Asp-Lys-D-Arg-D-His-Phe-Phe-D-Val-Tyr-Arg-Tyr-D-Tyr-Arg-His-Phe-$NH_2$
D-His-Glu-Lys-Tyr-D-Phe-Arg
D-His-Lys-Tyr-D-Phe-Glu-D-Asp-D-Asp-D-His-D-Lys-Arg-Trp-$NH_2$
D-Tyr-Trp-Lys-$NH_2$
Glu-Arg-D-Lys-Tyr-D-Val-Phe-D-His-Trp-Arg-D-Gly-Tyr-Arg-D-Met-$NH_2$
Gly-Ala-Lys-Phe-D-Lys-Glu-Arg-Tyr-His-D-Arg-D-Arg-Asp-Tyr-Trp-D-His-Trp-His-D-Lys-Asp.
Gly-D-Phe-Lys-His-D-Arg-Tyr-$NH_2$
His-Tyr-D-Arg-Trp-Lys-Phe-D-Asp-Ala-Arg-Cys-D-Tyr-His-Phe-D-Lys-Tyr-His-Ser-$NH_2$
Lys-D-Arg-Tyr-$NH_2$
Lys-D-Gln-Tyr-Arg-D-Phe-Trp-$NH_2$
Lys-Trp-D-Tyr-Arg-Asn-Phe-Tyr-D-His-$NH_2$
Met-Tyr-D-Arg-Phe-Arg-$NH_2$
Met-Tyr-D-Lys-Phe-Arg
Phe-Arg-D-His-Asp
Phe-D-Arg-2',6'-Dmt-Lys-$NH_2$
Phe-D-Arg-His
Phe-D-Arg-Lys-Trp-Tyr-D-Arg-His
Phe-D-Arg-Phe-Lys-$NH_2$
Phe-Phe-D-Tyr-Arg-Glu-Asp-D-Lys-Arg-D-Arg-His-Phe-$NH_2$
Phe-Tyr-Lys-D-Arg-Trp-His-D-Lys-D-Lys-Glu-Arg-D-Tyr-Thr
Thr-Gly-Tyr-Arg-D-His-Phe-Trp-D-His-Lys
Thr-Tyr-Arg-D-Lys-Trp-Tyr-Glu-Asp-D-Lys-D-Arg-His-Phe-D-Tyr-Gly-Val-Ile-D-His-Arg-Tyr-Lys-$NH_2$
Trp-D-Lys-Tyr-Arg-$NH_2$
Trp-Lys-Phe-D-Asp-Arg-Tyr-D-His-Lys
Tyr-Asp-D-Lys-Tyr-Phe-D-Lys-D-Arg-Phe-Pro-D-Tyr-His-Lys
Tyr-D-Arg-Phe-Lys-Glu-$NH_2$
Tyr-D-Arg-Phe-Lys-$NH_2$ -continued Tyr-D-His-Phe-D-Arg-Asp-Lys-D-Arg-His-Trp-D-His-Phe
Tyr-His-D-Gly-Met
Val-D-Lys-His-Tyr-D-Phe-Ser-Tyr-Arg-$NH_2$ In one embodiment, the peptides have mu-opioid receptor agonist activity (i.e., they activate the mu-opioid receptor). Mu-opioid activity can be assessed by radioligand binding to cloned mu-opioid receptors or by bioassays using the guinea pig ileum (Schiller et al., *Eur J Med Chem*, 35:895-901, 2000; Zhao et al., *J Pharmacol Exp Ther*, 307:947-954, 2003). Activation of the mu-opioid receptor typically elicits an analgesic effect. In certain instances, an aromatic-cationic peptide having mu-opioid receptor agonist activity is preferred. For example, during short-term treatment, such as in an acute disease or condition, it may be beneficial to use an aromatic-cationic peptide that activates the mu-opioid receptor. Such acute diseases and conditions are often associated with moderate or severe pain. In these instances, the analgesic effect of the aromatic-cationic peptide may be beneficial in the treatment regimen of the human patient or other mammal. An aromatic-cationic peptide which does not activate the mu-opioid receptor, however, may also be used with or without an analgesic, according to clinical requirements.

Alternatively, in other instances, an aromatic-cationic peptide that does not have mu-opioid receptor agonist activity is preferred. For example, during long-term treatment, such as in a chronic disease state or condition, the use of an aromatic-cationic peptide that activates the mu-opioid receptor may be contraindicated. In these instances, the potentially adverse or addictive effects of the aromatic-cationic peptide may preclude the use of an aromatic-cationic peptide that activates the mu-opioid receptor in the treatment regimen of a human patient or other mammal. Potential adverse effects may include sedation, constipation and respiratory depression. In such instances an aromatic-cationic peptide that does not activate the mu-opioid receptor may be an appropriate treatment.

Peptides which have mu-opioid receptor agonist activity are typically those peptides which have a tyrosine residue or a tyrosine derivative at the N-terminus (i.e., the first amino acid position). Suitable derivatives of tyrosine include 2'-methyltyrosine (Mmt); 2',6'-dimethyltyrosine (2',6'-Dmt); 3',5'-dimethyltyrosine (3'5'Dmt); N,2',6'-trimethyltyrosine (Tmt); and 2'-hydroxy-6'-methyltryosine (Hmt).

In one embodiment, a peptide that has mu-opioid receptor agonist activity has the formula Tyr-D-Arg-Phe-Lys-$NH_2$. This peptide has a net positive charge of three, contributed by the amino acids tyrosine, arginine, and lysine and has two aromatic groups contributed by the amino acids phenylalanine and tyrosine. The tyrosine can be a modified derivative of tyrosine such as in 2',6'-dimethyltyrosine to produce the compound having the formula 2',6'-Dmt-D-Arg-Phe-Lys-$NH_2$. This peptide has a molecular weight of 640 and carries a net three positive charge at physiological pH. The peptide readily penetrates the plasma membrane of several mammalian cell types in an energy-independent manner (Zhao et al., *J. Pharmacol Exp Ther.*, 304:425-432, 2003).

Peptides that do not have mu-opioid receptor agonist activity generally do not have a tyrosine residue or a derivative of tyrosine at the N-terminus (i.e., amino acid position 1). The amino acid at the N-terminus can be any naturally occurring or non-naturally occurring amino acid other than tyrosine. In one embodiment, the amino acid at the N-terminus is phenylalanine or its derivative. Exemplary derivatives of phenylalanine include 2'-methylphenylalanine (Mmp), 2',6'-dimethylphenylalanine (2',6'-Dmp), N,2',6'-trimethylphenylalanine (Tmp), and 2'-hydroxy-6'-methylphenylalanine (Hmp).

An example of an aromatic-cationic peptide that does not have mu-opioid receptor agonist activity has the formula Phe-D-Arg-Phe-Lys-NH$_2$. Alternatively, the N-terminal phenylalanine can be a derivative of phenylalanine such as 2',6'-dimethylphenylalanine (2',6'-Dmp). In one embodiment, a peptide with 2',6'-dimethylphenylalanine at amino acid position 1 has the formula 2',6'-Dmp-D-Arg-Phe-Lys-NH$_2$. In one embodiment, the amino acid sequence is rearranged such that Dmt is not at the N-terminus. An example of such an aromatic-cationic peptide that does not have mu-opioid receptor agonist activity has the formula D-Arg-2',6'-Dmt-Lys-Phe-NH$_2$.

The peptides mentioned herein and their derivatives can further include functional analogs. A peptide is considered a functional analog if the analog has the same function as the stated peptide. The analog may, for example, be a substitution variant of a peptide, wherein one or more amino acids are substituted by another amino acid. Suitable substitution variants of the peptides include conservative amino acid substitutions. Amino acids may be grouped according to their physicochemical characteristics as follows:

(a) Non-polar amino acids: Ala (A) Ser (S) Thr (T) Pro (P) Gly (G) Cys (C);
(b) Acidic amino acids: Asn (N) Asp (D) Glu (E) Gln (Q);
(c) Basic amino acids: His (H) Arg (R) Lys (K);
(d) Hydrophobic amino acids: Met (M) Leu (L) Ile (I) Val (V); and
(e) Aromatic amino acids: Phe (F) Tyr (Y) Trp (W) His (H).

Substitutions of an amino acid in a peptide by another amino acid in the same group is referred to as a conservative substitution and may preserve the physicochemical characteristics of the original peptide. In contrast, substitutions of an amino acid in a peptide by another amino acid in a different group is generally more likely to alter the characteristics of the original peptide.

Examples of peptides that activate mu-opioid receptors include, but are not limited to, the aromatic-cationic peptides shown in Table 5.

TABLE 5

Peptide Analogs with Mu-Opioid Activity

| Amino Acid Position 1 | Amino Acid Position 2 | Amino Acid Position 3 | Amino Acid Position 4 | C-Terminal Modification |
|---|---|---|---|---|
| Tyr | D-Arg | Phe | Lys | NH$_2$ |
| Tyr | D-Arg | Phe | Orn | NH$_2$ |
| Tyr | D-Arg | Phe | Dab | NH$_2$ |
| Tyr | D-Arg | Phe | Dap | NH$_2$ |
| 2'6'Dmt | D-Arg | Phe | Lys | NH$_2$ |
| 2'6'Dmt | D-Arg | Phe | Lys-NH(CH$_2$)$_2$—NH-dns | NH$_2$ |
| 2'6'Dmt | D-Arg | Phe | Lys-NH(CH$_2$)$_2$—NH-atn | NH$_2$ |
| 2'6'Dmt | D-Arg | Phe | dnsLys | NH$_2$ |
| 2'6'Dmt | D-Cit | Phe | Lys | NH$_2$ |
| 2'6'Dmt | D-Cit | Phe | Ahp | NH$_2$ |
| 2'6'Dmt | D-Arg | Phe | Orn | NH$_2$ |
| 2'6'Dmt | D-Arg | Phe | Dab | NH$_2$ |
| 2'6'Dmt | D-Arg | Phe | Dap | NH$_2$ |
| 2'6'Dmt | D-Arg | Phe | Ahp(2-aminoheptanoic acid) | NH$_2$ |
| Bio-2'6'Dmt | D-Arg | Phe | Lys | NH$_2$ |
| 3'5'Dmt | D-Arg | Phe | Lys | NH$_2$ |
| 3'5'Dmt | D-Arg | Phe | Orn | NH$_2$ |
| 3'5'Dmt | D-Arg | Phe | Dab | NH$_2$ |
| 3'5'Dmt | D-Arg | Phe | Dap | NH$_2$ |
| Tyr | D-Arg | Tyr | Lys | NH$_2$ |
| Tyr | D-Arg | Tyr | Orn | NH$_2$ |
| Tyr | D-Arg | Tyr | Dab | NH$_2$ |
| Tyr | D-Arg | Tyr | Dap | NH$_2$ |
| 2'6'Dmt | D-Arg | Tyr | Lys | NH$_2$ |
| 2'6'Dmt | D-Arg | Tyr | Orn | NH$_2$ |
| 2'6'Dmt | D-Arg | Tyr | Dab | NH$_2$ |
| 2'6'Dmt | D-Arg | Tyr | Dap | NH$_2$ |
| 2'6'Dmt | D-Arg | 2'6'Dmt | Lys | NH$_2$ |
| 2'6'Dmt | D-Arg | 2'6'Dmt | Orn | NH$_2$ |
| 2'6'Dmt | D-Arg | 2'6'Dmt | Dab | NH$_2$ |
| 2'6'Dmt | D-Arg | 2'6'Dmt | Dap | NH$_2$ |
| 3'5'Dmt | D-Arg | 3'5'Dmt | Arg | NH$_2$ |
| 3'5'Dmt | D-Arg | 3'5'Dmt | Lys | NH$_2$ |
| 3'5'Dmt | D-Arg | 3'5'Dmt | Orn | NH$_2$ |
| 3'5'Dmt | D-Arg | 3'5'Dmt | Dab | NH$_2$ |
| Tyr | D-Lys | Phe | Dap | NH$_2$ |
| Tyr | D-Lys | Phe | Arg | NH$_2$ |
| Tyr | D-Lys | Phe | Lys | NH$_2$ |
| Tyr | D-Lys | Phe | Orn | NH$_2$ |
| 2'6'Dmt | D-Lys | Phe | Dab | NH$_2$ |
| 2'6'Dmt | D-Lys | Phe | Dap | NH$_2$ |
| 2'6'Dmt | D-Lys | Phe | Arg | NH$_2$ |
| 2'6'Dmt | D-Lys | Phe | Lys | NH$_2$ |
| 3'5'Dmt | D-Lys | Phe | Orn | NH$_2$ |
| 3'5'Dmt | D-Lys | Phe | Dab | NH$_2$ |
| 3'5'Dmt | D-Lys | Phe | Dap | NH$_2$ |
| 3'5'Dmt | D-Lys | Phe | Arg | NH$_2$ |
| Tyr | D-Lys | Tyr | Lys | NH$_2$ |
| Tyr | D-Lys | Tyr | Orn | NH$_2$ |
| Tyr | D-Lys | Tyr | Dab | NH$_2$ |
| Tyr | D-Lys | Tyr | Dap | NH$_2$ |
| 2'6'Dmt | D-Lys | Tyr | Lys | NH$_2$ |
| 2'6'Dmt | D-Lys | Tyr | Orn | NH$_2$ |
| 2'6'Dmt | D-Lys | Tyr | Dab | NH$_2$ |
| 2'6'Dmt | D-Lys | Tyr | Dap | NH$_2$ |
| 2'6'Dmt | D-Lys | 2'6'Dmt | Lys | NH$_2$ |
| 2'6'Dmt | D-Lys | 2'6'Dmt | Orn | NH$_2$ |
| 2'6'Dmt | D-Lys | 2'6'Dmt | Dab | NH$_2$ |
| 2'6'Dmt | D-Lys | 2'6'Dmt | Dap | NH$_2$ |
| 2'6'Dmt | D-Arg | Phe | dnsDap | NH$_2$ |
| 2'6'Dmt | D-Arg | Phe | atnDap | NH$_2$ |
| 3'5'Dmt | D-Lys | 3'5'Dmt | Lys | NH$_2$ |
| 3'5'Dmt | D-Lys | 3'5'Dmt | Orn | NH$_2$ |
| 3'5'Dmt | D-Lys | 3'5'Dmt | Dab | NH$_2$ |
| 3'5'Dmt | D-Lys | 3'5'Dmt | Dap | NH$_2$ |
| Tyr | D-Lys | Phe | Arg | NH$_2$ |
| Tyr | D-Orn | Phe | Arg | NH$_2$ |
| Tyr | D-Dab | Phe | Arg | NH$_2$ |
| Tyr | D-Dap | Phe | Arg | NH$_2$ |
| 2'6'Dmt | D-Arg | Phe | Arg | NH$_2$ |
| 2'6'Dmt | D-Lys | Phe | Arg | NH$_2$ |
| 2'6'Dmt | D-Orn | Phe | Arg | NH$_2$ |
| 2'6'Dmt | D-Dab | Phe | Arg | NH$_2$ |
| 3'5'Dmt | D-Dap | Phe | Arg | NH$_2$ |
| 3'5'Dmt | D-Arg | Phe | Arg | NH$_2$ |
| 3'5'Dmt | D-Lys | Phe | Arg | NH$_2$ |
| 3'5'Dmt | D-Orn | Phe | Arg | NH$_2$ |
| Tyr | D-Lys | Tyr | Arg | NH$_2$ |
| Tyr | D-Orn | Tyr | Arg | NH$_2$ |
| Tyr | D-Dab | Tyr | Arg | NH$_2$ |
| Tyr | D-Dap | Tyr | Arg | NH$_2$ |
| 2'6'Dmt | D-Arg | 2'6'Dmt | Arg | NH$_2$ |
| 2'6'Dmt | D-Lys | 2'6'Dmt | Arg | NH$_2$ |
| 2'6'Dmt | D-Orn | 2'6'Dmt | Arg | NH$_2$ |
| 2'6'Dmt | D-Dab | 2'6'Dmt | Arg | NH$_2$ |
| 3'5'Dmt | D-Dap | 3'5'Dmt | Arg | NH$_2$ |
| 3'5'Dmt | D-Arg | 3'5'Dmt | Arg | NH$_2$ |
| 3'5'Dmt | D-Lys | 3'5'Dmt | Arg | NH$_2$ |
| 3'5'Dmt | D-Orn | 3'5'Dmt | Arg | NH$_2$ |

TABLE 5-continued

Peptide Analogs with Mu-Opioid Activity

| Amino Acid Position 1 | Amino Acid Position 2 | Amino Acid Position 3 | Amino Acid Position 4 | C-Terminal Modification |
|---|---|---|---|---|
| Mmt | D-Arg | Phe | Lys | NH$_2$ |
| Mmt | D-Arg | Phe | Orn | NH$_2$ |
| Mmt | D-Arg | Phe | Dab | NH$_2$ |
| Mmt | D-Arg | Phe | Dap | NH$_2$ |
| Tmt | D-Arg | Phe | Lys | NH$_2$ |
| Tmt | D-Arg | Phe | Orn | NH$_2$ |
| Tmt | D-Arg | Phe | Dab | NH$_2$ |
| Tmt | D-Arg | Phe | Dap | NH$_2$ |
| Hmt | D-Arg | Phe | Lys | NH$_2$ |
| Hmt | D-Arg | Phe | Orn | NH$_2$ |
| Hmt | D-Arg | Phe | Dab | NH$_2$ |
| Hmt | D-Arg | Phe | Dap | NH$_2$ |
| Mmt | D-Lys | Phe | Lys | NH$_2$ |
| Mmt | D-Lys | Phe | Orn | NH$_2$ |
| Mmt | D-Lys | Phe | Dab | NH$_2$ |
| Mmt | D-Lys | Phe | Dap | NH$_2$ |
| Mmt | D-Lys | Phe | Arg | NH$_2$ |
| Tmt | D-Lys | Phe | Lys | NH$_2$ |
| Tmt | D-Lys | Phe | Orn | NH$_2$ |
| Tmt | D-Lys | Phe | Dab | NH$_2$ |
| Tmt | D-Lys | Phe | Dap | NH$_2$ |
| Tmt | D-Lys | Phe | Arg | NH$_2$ |
| Hmt | D-Lys | Phe | Lys | NH$_2$ |
| Hmt | D-Lys | Phe | Orn | NH$_2$ |
| Hmt | D-Lys | Phe | Dab | NH$_2$ |
| Hmt | D-Lys | Phe | Dap | NH$_2$ |
| Hmt | D-Lys | Phe | Arg | NH$_2$ |
| Mmt | D-Lys | Phe | Arg | NH$_2$ |
| Mmt | D-Orn | Phe | Arg | NH$_2$ |
| Mmt | D-Dab | Phe | Arg | NH$_2$ |
| Mmt | D-Dap | Phe | Arg | NH$_2$ |
| Mmt | D-Arg | Phe | Arg | NH$_2$ |
| Tmt | D-Lys | Phe | Arg | NH$_2$ |
| Tmt | D-Orn | Phe | Arg | NH$_2$ |
| Tmt | D-Dab | Phe | Arg | NH$_2$ |
| Tmt | D-Dap | Phe | Arg | NH$_2$ |
| Tmt | D-Arg | Phe | Arg | NH$_2$ |
| Hmt | D-Lys | Phe | Arg | NH$_2$ |
| Hmt | D-Orn | Phe | Arg | NH$_2$ |
| Hmt | D-Dab | Phe | Arg | NH$_2$ |
| Hmt | D-Dap | Phe | Arg | NH$_2$ |
| Hmt | D-Arg | Phe | Arg | NH$_2$ |

Dab = diaminobutyric
Dap = diaminopropionic acid
Dmt = dimethyltyrosine
Mmt = 2'-methyltyrosine
Tmt = N,2',6'-trimethyltyrosine
Hmt = 2'-hydroxy,6'-methyltyrosine
dnsDap = β-dansyl-L-α,β-diaminopropionic acid
atnDap = β-anthraniloyl-L-α,β-diaminopropionic acid
Bio = biotin Examples of analogs that do not activate mu-opioid receptors include, but are not limited to, the aromatic-cationic peptides shown in Table 6.

TABLE 6

Peptide Analogs Lacking Mu-Opioid Activity

| Amino Acid Position 1 | Amino Acid Position 2 | Amino Acid Position 3 | Amino Acid Position 4 | C-Terminal Modification |
|---|---|---|---|---|
| D-Arg | Dmt | Lys | Phe | NH$_2$ |
| D-Arg | Dmt | Phe | Lys | NH$_2$ |
| D-Arg | Phe | Lys | Dmt | NH$_2$ |
| D-Arg | Phe | Dmt | Lys | NH$_2$ |
| D-Arg | Lys | Dmt | Phe | NH$_2$ |
| D-Arg | Lys | Phe | Dmt | NH$_2$ |
| Phe | Lys | Dmt | D-Arg | NH$_2$ |
| Phe | Lys | D-Arg | Dmt | NH$_2$ |
| Phe | D-Arg | Phe | Lys | NH$_2$ |
| Phe | D-Arg | Dmt | Lys | NH$_2$ |
| Phe | D-Arg | Lys | Dmt | NH$_2$ |
| Phe | Dmt | D-Arg | Lys | NH$_2$ |
| Phe | Dmt | Lys | D-Arg | NH$_2$ |
| Lys | Phe | D-Arg | Dmt | NH$_2$ |
| Lys | Phe | Dmt | D-Arg | NH$_2$ |
| Lys | Dmt | D-Arg | Phe | NH$_2$ |
| Lys | Dmt | Phe | D-Arg | NH$_2$ |
| Lys | D-Arg | Phe | Dmt | NH$_2$ |
| Lys | D-Arg | Dmt | Phe | NH$_2$ |
| D-Arg | Dmt | D-Arg | Phe | NH$_2$ |
| D-Arg | Dmt | D-Arg | Dmt | NH$_2$ |
| D-Arg | Dmt | D-Arg | Tyr | NH$_2$ |
| D-Arg | Dmt | D-Arg | Trp | NH$_2$ |
| Trp | D-Arg | Phe | Lys | NH$_2$ |
| Trp | D-Arg | Tyr | Lys | NH$_2$ |
| Trp | D-Arg | Trp | Lys | NH$_2$ |
| Trp | D-Arg | Dmt | Lys | NH$_2$ |
| D-Arg | Trp | Lys | Phe | NH$_2$ |
| D-Arg | Trp | Phe | Lys | NH$_2$ |
| D-Arg | Trp | Lys | Dmt | NH$_2$ |
| D-Arg | Trp | Dmt | Lys | NH$_2$ |
| D-Arg | Lys | Trp | Phe | NH$_2$ |
| D-Arg | Lys | Trp | Dmt | NH$_2$ |
| Cha | D-Arg | Phe | Lys | NH$_2$ |
| Ala | D-Arg | Phe | Lys | NH$_2$ |

Cha = cyclohexyl alanine

The amino acids of the peptides shown in Table 5 and 6 may be in either the L- or the D-configuration.

The peptides may be synthesized by any of the methods well known in the art. Suitable methods for chemically synthesizing the protein include, for example, those described by Stuart and Young in *Solid Phase Peptide Synthesis*, Second Edition, Pierce Chemical Company (1984), and in *Methods Enzymol.*, 289, Academic Press, Inc, New York (1997).

Prophylactic and Therapeutic Uses of Aromatic-Cationic Peptides.

General.

The aromatic-cationic peptides described herein, such as D-Arg-2',6'-Dmt-Lys-Phe-NH$_2$, or pharmaceutically acceptable salts thereof, such as acetate salt or trifluoroacetate salt, are useful to prevent or treat a disease or condition. Specifically, the disclosure provides for both prophylactic and therapeutic methods of treating a subject at risk of (or susceptible to) vessel occlusion injury, an anatomic zone of no re-flow or cardiac ischemia-reperfusion injury. Accordingly, the present methods provide for the prevention and/or treatment of vessel occlusion injury, cardiac ischemia-reperfusion injury or an anatomic zone of no-reflow in a subject by administering an effective amount of an aromatic-cationic peptide to a subject in need thereof.

Determination of the Biological Effect of the Aromatic-Cationic Peptide-Based Therapeutic.

In various embodiments, suitable in vitro or in vivo assays are performed to determine the effect of a specific aromatic-cationic peptide-based therapeutic and whether its administration is indicated for treatment. In various embodiments, in vitro assays can be performed with representative animal models, to determine if a given aromatic-cationic peptide-based therapeutic exerts the desired effect in preventing or treating an anatomic zone of no re-flow. Compounds for use in therapy can be tested in suitable animal model systems including, but not limited to rats, mice, chicken, pigs, cows, monkeys, rabbits, sheep, guinea pig, and the like, prior to testing in human subjects. Similarly, for in vivo testing, any of the animal model systems known in the art can be used prior to administration to human subjects.

Prophylactic Methods.

In one aspect, the invention provides a method for preventing, in a subject an anatomic zone of no re-flow by administering to the subject an aromatic-cationic peptide that prevents the initiation or progression of the condition. Subjects at risk for an anatomic zone of no re-flow can be identified by, e.g., any or a combination of diagnostic or prognostic assays as described herein. In prophylactic applications, pharmaceutical compositions or medicaments of aromatic-cationic peptides are administered to a subject susceptible to, or otherwise at risk of a disease or condition in an amount sufficient to eliminate or reduce the risk, lessen the severity, or delay the outset of the disease or condition, including biochemical, histologic and/or behavioral symptoms of the disease or condition, its complications and intermediate pathological phenotypes presenting during development of the disease or condition. Administration of a prophylactic aromatic-cationic can occur prior to the manifestation of symptoms characteristic of the aberrancy, such that a disease or disorder is prevented or, alternatively, delayed in its progression. The appropriate compound can be determined based on screening assays described above.

Therapeutic Methods.

Another aspect of the technology includes methods of treating vessel occlusion injury, an anatomic zone of no re-flow or cardiac ischemia-reperfusion injury in a subject for therapeutic purposes. In therapeutic applications, compositions or medicaments are administered to a subject suspected of, or already suffering from such a disease or condition in an amount sufficient to cure, or at least partially arrest, the symptoms of the disease or condition, including its complications and intermediate pathological phenotypes in development of the disease. or condition As such, the invention provides methods of treating an individual afflicted with an anatomic zone of no re-flow.

Modes of Administration and Effective Dosages

Any method known to those in the art for contacting a cell, organ or tissue with a peptide may be employed. Suitable methods include in vitro, ex vivo, or in vivo methods. In vivo methods typically include the administration of an aromatic-cationic peptide, such as those described above, to a mammal, suitably a human. When used in vivo for therapy, the aromatic-cationic peptides are administered to the subject in effective amounts (i.e., amounts that have desired therapeutic effect). The dose and dosage regimen will depend upon the degree of the injury in the subject, the characteristics of the particular aromatic-cationic peptide used, e.g., its therapeutic index, the subject, and the subject's history.

The effective amount may be determined during preclinical trials and clinical trials by methods familiar to physicians and clinicians. An effective amount of a peptide useful in the methods may be administered to a mammal in need thereof by any of a number of well-known methods for administering pharmaceutical compounds. The peptide may be administered systemically or locally.

The peptide may be formulated as a pharmaceutically acceptable salt. The term "pharmaceutically acceptable salt" means a salt prepared from a base or an acid which is acceptable for administration to a patient, such as a mammal (e.g., salts having acceptable mammalian safety for a given dosage regime). However, it is understood that the salts are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a peptide contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucoronic, mandelic, mucic, nicotinic, orotic, pamoic, pantothenic, sulfonic acids (e.g., benzenesulfonic, camphorsulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like. In some embodiments, the salt is an acetate salt or a trifluoroacetate salt.

The aromatic-cationic peptides described herein, such as D-Arg-2',6'-Dmt-Lys-Phe-NH$_2$, or pharmaceutically acceptable salts thereof, such as acetate salt or trifluoroacetate salt, can be incorporated into pharmaceutical compositions for administration, singly or in combination, to a subject for the treatment or prevention of a disorder described herein. Such compositions typically include the active agent and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment (e.g., vials of drug, vials of diluent, syringes and needles) for a treatment course (e.g., 7 days of treatment).

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

The aromatic-cationic peptide compositions can include a carrier, which can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, it were preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressurized container or dispenser which contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In one embodiment, transdermal administration may be performed my iontophoresis.

A therapeutic protein or peptide can be formulated in a carrier system. The carrier can be a colloidal system. The colloidal system can be a liposome, a phospholipid bilayer vehicle. In one embodiment, the therapeutic peptide is encapsulated in a liposome while maintaining peptide integrity. As one skilled in the art would appreciate, there are a variety of methods to prepare liposomes. (See Lichtenberg et al., *Methods Biochem. Anal.*, 33:337-462 (1988); Anselem et al., *Liposome Technology*, CRC Press (1993)). Liposomal formulations can delay clearance and increase cellular uptake (See Reddy, *Ann. Pharmacother.*, 34(7-8):915-923 (2000)). An active agent can also be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

The carrier can also be a polymer, e.g., a biodegradable, biocompatible polymer matrix. In one embodiment, the therapeutic peptide can be embedded in the polymer matrix, while maintaining protein integrity. The polymer may be natural, such as polypeptides, proteins or polysaccharides, or synthetic, such as poly α-hydroxy acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect. (See Reddy, *Ann. Pharmacother.*, 34(7-8):915-923 (2000)). A polymer formulation for human growth hormone (hGH) has been used in clinical trials. (See Kozarich and Rich, *Chemical Biology*, 2:548-552 (1998)).

Examples of polymer microsphere sustained release formulations are described in PCT publication WO 99/15154 (Tracy et al.), U.S. Pat. Nos. 5,674,534 and 5,716,644 (both to Zale et al.), PCT publication WO 96/40073 (Zale et al.), and PCT publication WO 00/38651 (Shah et al.). U.S. Pat. Nos. 5,674,534 and 5,716,644 and PCT publication WO 96/40073 describe a polymeric matrix containing particles of erythropoietin that are stabilized against aggregation with a salt.

In some embodiments, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylacetic acid. Such formulations can be prepared using known techniques. The materials can also be obtained commercially, e.g., from Alza Corporation and Nova Pharmaceuticals, Inc. Liposomal suspensions (including liposomes targeted to specific cells with monoclonal antibodies to cell-specific antigens) can also be used as pharmaceutically acceptable carriers. These can be prepared according to methods known to those skilled in the art, for example, as described in U.S. Pat. No. 4,522,811.

The therapeutic compounds can also be formulated to enhance intracellular delivery. For example, liposomal delivery systems are known in the art, see, e.g., Chonn and Cullis, "Recent Advances in Liposome Drug Delivery Systems," *Current Opinion in Biotechnology* 6:698-708 (1995); Weiner, "Liposomes for Protein Delivery: Selecting Manufacture and Development Processes," *Immunomethods*, 4(3): 201-9 (1994); and Gregoriadis, "Engineering Liposomes for Drug Delivery: Progress and Problems," *Trends Biotechnol.*, 13(12):527-37 (1995). Mizguchi et al., *Cancer Lett.*, 100: 63-69 (1996), describes the use of fusogenic liposomes to deliver a protein to cells both in vivo and in vitro.

Dosage, toxicity and therapeutic efficacy of the therapeutic agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Typically, an effective amount of the aromatic-cationic peptides, sufficient for achieving a therapeutic or prophylactic effect, range from about 0.000001 mg per kilogram body weight per day to about 10,000 mg per kilogram body weight per day. Preferably, the dosage ranges are from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In one embodiment, a single dosage of peptide ranges from 0.1-10,000 micrograms per kg body weight. In one embodiment, aromatic-cationic peptide concentrations in a carrier range from 0.2 to 2000 micrograms per delivered milliliter. An exemplary treatment regime entails administration once per day or once a week. In therapeutic applications, a relatively high dosage at relatively short intervals is sometimes required until progression of the disease is reduced or terminated, and preferably until the subject shows partial or complete amelioration of symptoms of disease. Thereafter, the patient can be administered a prophylactic regime.

In some embodiments, a therapeutically effective amount of an aromatic-cationic peptide may be defined as a concentration of peptide at the target tissue of $10^{-12}$ to $10^{-6}$ molar, e.g., approximately $10^{-7}$ molar. This concentration may be delivered by systemic doses of 0.01 to 100 mg/kg or equivalent dose by body surface area. The schedule of doses would be optimized to maintain the therapeutic concentration at the target tissue, most preferably by single daily or weekly administration, but also including continuous administration (e.g., parenteral infusion or transdermal application).

In some embodiments, the dosage of the aromatic-cationic peptide is provided at a "low," "mid," or "high" dose level. In one embodiment, the low dose is provided from about 0.01 to about 0.5 mg/kg/h, suitably from about 0.0001 to about 0.1 mg/kg/h. In one embodiment, the mid-dose is provided from about 0.001 to about 1.0 mg/kg/h, suitably from about 0.01 to about 0.5 mg/kg/h. In one embodiment, the high dose is provided from about 0.005 to about 10 mg/kg/h, suitably from about 0.01 to about 2 mg/kg/h.

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

The mammal treated in accordance present methods can be any mammal, including, for example, farm animals, such as sheep, pigs, cows, and horses; pet animals, such as dogs and cats; laboratory animals, such as rats, mice and rabbits. In a suitable embodiment, the mammal is a human.

Measurement of the Anatomic Zone of No-Reflow

Imaging techniques are useful in assessing the effect of the peptides of the present technology on the anatomic zone of no re-flow. (See generally reference nos. 1-51). Re-flow phenomenon may be assessed using myocardial contrast echocardiography, coronary angiography, myocardial blush, coronary doppler imaging, electrocardiograph, nuclear imaging single-photon emission CT, using thallium or technetium-99m, and PET. Contrast-enhanced MRI can evaluate myocardial perfusion during first pass of the contrast agent. Alternatively, delayed contrast-enhanced MRI 20 min after contrast injection can be used to detect necrosis. The detection of hypoenhancement zones on first-pass perfusion MRI, which represents no re-flow, is associated with permanent dysfunction at follow-up. In some embodiments, microvascular obstructions can be assessed using cardiac MRI. For example, a 1.5-T body MRI scanner can be used to perform cardiac MRI in order to assess ventricular function, myocardial edema (area at risk), microvascular obstruction and infarct size.

EXAMPLES

The present invention is further illustrated by the following example, which should not be construed as limiting in any way.

As noted above, ischemia can result in significant changes in the microvasculature that interferes with normal blood flow to many tissues/organs. As such, the no-reflow phenomenon can occur in a variety of tissues/organs including heart, liver, brain, skin, skeletal muscle, kidney, etc. It is predicted that the aromatic-cationic peptides of the present technology are useful methods to prevent or treat the zone of anatomic no-reflow in a variety of tissues/organs.

Example 1. Effects of D-Ara-2',6'-Dmt-Lys-Phe-NH$_2$ on the Anatomic Zone of No-Reflow, Zone of Hemorrhage and Infarct Size Following Ischemia/Reperfusion Insult in the Rabbit Heart General.

The effects of D-Arg-2',6'-Dmt-Lys-Phe-NH$_2$ on infarct size and no-reflow after regional myocardial ischemia (approximately 30 min) and reperfusion (approximately 3 h) are studied. The efficacy of the study articles (i.e., vehicle/placebo and D-Arg-2',6'-Dmt-Lys-Phe-NH$_2$ (acetate salt)) are assessed with experimental procedures that differ by the time point of study article administration relative to the onset of ischemia and subsequent myocardial reperfusion.

Route and Duration of Administration.

The vehicle/placebo and D-Arg-2',6'-Dmt-Lys-Phe-NH$_2$ (acetate salt) are administered via intravenous infusion. Details regarding infusion and duration of infusion are provided in FIG. 1.

Test Animals.

Animals utilized in the studies are detailed in Table 7. Animals are maintained in animal facility in accordance with standards set by the USDA and NIH. Prior to randomization into the Protocol, rabbits are examined by qualified personnel and acclimated for a period of at least 2 days. All rabbits are observed daily for signs of diarrhea, lack of appetite, malaise and the like. If any of these signs are seen, the rabbit is not included in the study population. Animals are fasted (removal of food) overnight immediately prior to that animal's experiment. All animals are absent of obvious clinical disease. Body weights are recorded for each rabbit either the day before that animal's experiment or the day of that animal's experiment for the purpose of dose formulation calculation and anesthesia. Following the completion of each experiment, animals (already fully anesthetized) are euthanatized and disposed of appropriately.

TABLE 7

Description of Test Animals

| | |
|---|---|
| Species | Rabbits |
| Strain | New Zealand White |
| Sex | Male |
| Number of animals | Approximately 30-50 |
| Age at start of study | Approximately 4-7 months |
| Weight at start of study | Approximately 2.0-3.75 kilograms |

Study Articles (D-Arg-2',6'-Dmt-Lys-Phe-N$_H$(Acetate Salt) and Vehicle/Placebo).

The lot number, supplier name, peptide content, expiration date, and storage condition of the study articles described below are recorded. The study article formulations for D-Arg-2',6'-Dmt-Lys-Phe-NH$_2$ (acetate salt) are prepared as weight-to-volume mixtures in vehicle as detailed below.

D-Arg-2',6'-Dmt-Lys-Phe-NH$_2$ (acetate salt) (sterile lyophilized powder) used in these studies is supplied by Stealth Peptides, Inc. D-Arg-2',6'-Dmt-Lys-Phe-NH$_2$ (acetate salt) study article is dissolved in the sterile normal saline (0.9% NaCl) to make an D-Arg-2',6'-Dmt-Lys-Phe-NH$_2$ (acetate salt) study article stock solution. After reconstitution with saline, the D-Arg-2',6'-Dmt-Lys-Phe-NH$_2$ (acetate salt) study article stock solution is filtered using a sterile filter unit with a membrane of less than 0.22 µm (a PES or PVDF membrane) and stored at −20° C. until use.

On the morning of each D-Arg-2',6'-Dmt-Lys-Phe-NH$_2$ (acetate salt) experiment, the aliquoted frozen D-Arg-2',6'-Dmt-Lys-Phe-NH$_2$ (acetate salt) study article stock solution is thawed at room temperature before mixing it with sterile normal saline (0.9% NaCl). The vehicle/placebo is sterile normal saline (0.9% NaCl). The concentration/dose of D-Arg-2',6'-Dmt-Lys-Phe-NH$_2$ (acetate salt) to be used in the studies is summarized in Tables 8-11 for dosing solution preparation and infusion rates.

TABLE 8

Dosing Preparation for D-Arg-2',6'-Dmt-Lys-Phe-NH$_2$

| | |
|---|---|
| Test article | D-Arg-2',6'-Dmt-Lys-Phe-NH$_2$ (acetate salt) |
| Vehicle | Sterile saline (0.9% NaCl) |
| Study Group | Group 1: 0.05 mg/kg/hr of D-Arg-2',6'-Dmt-Lys-Phe-NH$_2$ (acetate salt), infusion for the entire 200 minutes (20' ischemia + 180' reperfusion) |
| | Group 2: 0.075 mg/kg/hr of D-Arg-2',6'-Dmt-Lys-Phe-NH$_2$ (acetate salt), infusion for the first 20 minutes, then change to 0.05 mg/kg/hr of D-Arg-2',6'-Dmt-Lys-Phe-NH$_2$ (acetate salt), infusion for 170 minutes. Total infusion time = 190 minutes (10' ischemia + 180 min reperfusion) |
| | Group 3: 0.10 mg/kg/hr of D-Arg-2',6'-Dmt-Lys-Phe-NH$_2$ (acetate salt), infusion for the first 20 minutes, then switch to 0.05 mg/kg/hr of D-Arg-2',6'-Dmt-Lys-Phe-NH$_2$ (acetate salt), infusion for 160 minutes. Total infusion time is equal to 180 minutes (180 min reperfusion only) |

TABLE 9

Dosing Preparation for D-Arg-2',6'-Dmt-Lys-Phe-NH$_2$
For Group 1: 0.05 mg/kg/hr infusion for 200 minutes

| Infusion schedule | Dose (mg/kg/hr) | Peptide conc. (mg/mL) | Body weight (kg) | Infusion rate (mL/min) | Infusion rate (mL/hr) | Total infusion volume (mL) |
|---|---|---|---|---|---|---|
| From 0' to 200' | 0.050 | 0.10 | 2.0 | 0.017 | 1.00 | 3.3 |
|  | 0.050 | 0.10 | 2.5 | 0.021 | 1.25 | 4.2 |
|  | 0.050 | 0.10 | 3.0 | 0.025 | 1.50 | 5.0 |
|  | 0.050 | 0.10 | 3.5 | 0.029 | 1.75 | 5.8 |
|  | 0.050 | 0.10 | 4.0 | 0.033 | 2.00 | 6.7 |

TABLE 10

Dosing Preparation for D-Arg-2',6'-Dmt-Lys-Phe-NH$_2$ For Group 2: 0.075 mg/kg/hr infusion for 20 minutes; switch to 0.05 mg/kg/hr for 170 minutes. Total infusion time = 190 minutes

| Infusion Schedule | Dose (mg/kg/hr) | Peptide Conc. (mg/mL) | Body weight (kg) | Infusion rate (mL/min) | Infusion rate (mL/hr) | Infusion volume (mL) | Total infusion volume (mL) |
|---|---|---|---|---|---|---|---|
| From 0' to 20' | 0.075 | 0.10 | 2.0 | 0.025 | 1.50 | 0.50 | 3.3 |
| From 21' to 190' | 0.050 | 0.10 | 2.0 | 0.017 | 1.00 | 2.83 |  |
| From 0' to 20' | 0.075 | 0.10 | 2.5 | 0.031 | 1.88 | 0.63 | 4.2 |
| From 21' to 190' | 0.050 | 0.10 | 2.5 | 0.021 | 1.25 | 3.54 |  |
| From 0' to 20' | 0.075 | 0.10 | 3.0 | 0.038 | 2.25 | 0.75 | 5.0 |
| From 21' to 190' | 0.050 | 0.10 | 3.0 | 0.025 | 1.50 | 4.25 |  |
| From 0' to 20' | 0.075 | 0.10 | 3.5 | 0.044 | 2.63 | 0.88 | 5.8 |
| From 21' to 190' | 0.050 | 0.10 | 3.5 | 0.029 | 1.75 | 4.96 |  |
| From 0' to 20' | 0.075 | 0.10 | 4.0 | 0.050 | 3.00 | 1.00 | 6.7 |
| From 21' to 190' | 0.050 | 0.10 | 4.0 | 0.033 | 2.00 | 5.67 |  |

TABLE 11

Dosing Preparation for D-Arg-2',6'-Dmt-Lys-Phe-NH$_2$ For Group 3: 0.10 mg/kg/hr infusion for 20 minutes; switch to 0.05 mg/kg/hr for 160 minutes. Total infusion time = 180 minutes (180' reperfusion only)

| Infusion Schedule | Dose (mg/kg/hr) | Peptide Conc. (mg/mL) | Body weight (kg) | Infusion rate (mL/min) | Infusion rate (mL/hr) | Infusion volume (mL) | Total infusion volume (mL) |
|---|---|---|---|---|---|---|---|
| From 0' to 20' | 0.100 | 0.10 | 2.0 | 0.033 | 2.00 | 0.67 | 3.3 |
| From 21' to 190' | 0.050 | 0.10 | 2.0 | 0.017 | 1.00 | 2.67 |  |
| From 0' to 20' | 0.100 | 0.10 | 2.5 | 0.042 | 2.50 | 0.83 | 4.2 |
| From 21' to 190' | 0.050 | 0.10 | 2.5 | 0.021 | 1.25 | 3.33 |  |
| From 0' to 20' | 0.100 | 0.10 | 3.0 | 0.050 | 3.00 | 1.00 | 5.0 |
| From 21' to 190' | 0.050 | 0.10 | 3.0 | 0.025 | 1.50 | 4.00 |  |
| From 0' to 20' | 0.100 | 0.10 | 3.5 | 0.058 | 3.50 | 1.17 | 5.8 |
| From 21' to 190' | 0.050 | 0.10 | 3.5 | 0.029 | 1.75 | 4.67 |  |
| From 0' to 20' | 0.100 | 0.10 | 4.0 | 0.067 | 4.00 | 1.33 | 6.7 |
| From 21' to 190' | 0.050 | 0.10 | 4.0 | 0.033 | 2.00 | 5.33 |  |

Study Design.

Studies are designed utilizing an adaptive design model. As such, the data collected in the first group of approximately 32 rabbits (Cohort 1) is used to modify, where appropriate, the remainder of the studies (e.g., subsequent cohorts). After approximately 15-30 min of stabilization, baseline hemodynamic parameters and temperatures are obtained. Furthermore, the rabbits are randomized to one of the following four groups (see FIG. 1): Group 1, Study article D-Arg-2',6'-Dmt-Lys-Phe-NH$_2$ (acetate salt): D-Arg-2',6'-Dmt-Lys-Phe-NH$_2$ (acetate salt) infusion starting at approximately 10 minutes after coronary artery occlusion (CAO) and continuing throughout approximately 180 minutes of reperfusion, n=8 (dose/volume to be determined); D-Arg-2',6'-Dmt-Lys-Phe-NH$_2$ (acetate salt) infusion time is equal to approximately 200 minutes; Group 2, Study article D-Arg-2',6'-Dmt-Lys-Phe-NH$_2$ (acetate salt): D-Arg-2',6'-Dmt-Lys-Phe-NH$_2$ (acetate salt) infusion starting approximately 20 minutes after CAO, (10 minutes before reperfusion) and continuing throughout approximately 180 minutes of reperfusion, n=8 (dose/volume to be determined); D-Arg-2',6'-Dmt-Lys-Phe-NH$_2$ (acetate salt) infusion time is equal to approximately 190 minutes; Group 3, Study article D-Arg-2',6'-Dmt-Lys-Phe-NH$_2$ (acetate salt): D-Arg-2',6'-Dmt-Lys-Phe-NH$_2$ (acetate salt) starting immediately prior to coronary artery reperfusion and continuing throughout approximately 180 minutes of reperfusion, n=8 (dose/volume to be determined); D-Arg-2',6'-Dmt-Lys-Phe-NH$_2$ (acetate salt) infusion time is equal to approximately 180 minutes; and Group 4, Study article (control): An equivalent volume relative to D-Arg-2',6'-Dmt-Lys-Phe-NH$_2$ (acetate salt) of vehicle/placebo infusion starting at approximately 10 minutes after CAO and continuing throughout approximately 180 minutes of reperfusion, n=8. Vehicle/placebo infusion time is equal to approximately 200 minutes.

To achieve desired plasma concentrations with D-Arg-2',6'-Dmt-Lys-Phe-NH$_2$ for specific time points (e.g., upon reperfusion, 15 minutes after reperfusion begins and approximately steady state), the dosing design for each of Groups 1, 2 and 3 should be as follows:

Group 1, 0.05 mg/kg/hr of D-Arg-2',6'-Dmt-Lys-Phe-NH$_2$ (acetate salt), infusion for the entire 200 minutes of Group 1, Group 2, 0.075 mg/kg/hr of D-Arg-2',6'-Dmt-Lys-Phe-NH$_2$ (acetate salt), infusion for the first 20 minutes, then change to 0.05 mg/kg/hr of D-Arg-2',6'-Dmt-Lys-Phe-NH$_2$ (acetate salt), infusion for 170 minutes of Group 2, and Group 3, 0.10 mg/kg/hr of D-Arg-2',6'-Dmt-Lys-Phe-NH$_2$ (acetate salt), infusion for the first 20 minutes, then change to 0.05 mg/kg/hr of D-Arg-2',6'-Dmt-Lys-Phe-NH$_2$ (acetate salt), infusion for 160 minutes of Group 3.

Surgical Preparation (See FIG. 2A: Study Flow Chart—In-Vivo Procedures and FIG. 2B: Study Flow Chart—Pathologic Measurements).

Male New Zealand White rabbits are anesthetized with an intramuscular injection of a mixture of ketamine (approximately 75 mg/kg) and xylazine (approximately 5 mg/kg). Pentobarbital anesthesia are given intravenously during the study as required to maintain a deep level of anesthesia. The rabbits are intubated and mechanically ventilated with oxygen-enriched air. Fluid-filled catheters are inserted into the left jugular vein to administer the study articles, into the right jugular vein to administer anesthesia, and into the left carotid artery to assess hemodynamics and to take a reference blood sample during regional myocardial blood flow measurement. The chest are opened through the left fourth intercostal space, the pericardium incised, and the heart exposed. Near the base of the heart, the first large antero-lateral branch of the circumflex artery, or the circumflex artery itself, are encircled with a 4-O silk suture. CAO in this region normally results in ischemia of a large territory of the antero-lateral and apical ventricular wall. The ends of the suture are threaded through a piece of tubing, forming a snare that are tightened to occlude the artery. A catheter is placed into the left atrial appendage to inject radioactive microspheres, and dyes at the end of the study. A temperature probe is inserted into the rectum, and body temperature is maintained using a heating pad. All rabbits will undergo approximately 30 minutes of CAO and reperfusion for approximately 3 hours. Regional myocardial blood flow, using the radioactive microsphere technique, are measured at approximately 20-30 minutes of CAO to ensure ischemia in the risk zone and that the degree of ischemia are equivalent in the four groups.

Route and Duration of Study Articles.

Pump infusion rate and volume are calibrated before initiation of the study. The study articles are administered via the jugular catheter using an infusion pump at rates to be determined. Infusion at the time appropriate for the particular group and continue throughout approximately 180 minutes of reperfusion.

Data Procedures, Collection, and Measurements.

Heart rate, systolic and diastolic pressures, and rectal temperature are monitored and recorded at approximately baseline, 5, 15 and 29 minutes of occlusion, and at approximately 5, 15, 30, 60, 90, 120, 150 and 180 minutes of reperfusion. These times points may vary slightly to account for the stability or instability of the animal.

At approximately 180 minutes, approximately 1 ml/kg of a ~4% solution of thioflavin S is injected into the heart via the left atrial catheter to define the region of no-reflow. Thioflavin S, a fluorescent green-yellow dye, stains endothelium, and serves as a marker of perfusion. Thioflavin S is used as a standard marker for identifying zones of no-reflow (See FIG. 3). The coronary artery is re-occluded and the ischemic risk region delineated with approximately 4 ml of a ~50% solution of Unisperse blue dye (supplier Ciba Geigy) injected into the left atrium.

Regional Myocardial Blood Flow Technique (RMBF).

RMBF are measured at approximately 25 minutes of ischemia using approximately 2×10$^6$ radioactive microspheres (supplier PerkinElmer Life Sciences). The microspheres are injected into the left atrium through the left atrial catheter, and a reference blood sample are obtained from the carotid artery at the rate of approximately 2.06 ml/min. At the end of the Protocol, samples are cut from the risk region (determined by the absence of blue dye) and from the non-ischemic region. The samples are weighed and counted together with the reference blood samples in a computerized gamma well counter (supplier Canberra, System S100). After appropriate subtraction of backgrounds and correction for overlapping radioactivity between isotopes, RMBF are computed and the results are expressed as ml/min/g (See FIG. 3).

Hemodynamic Measurements.

Heart rate and blood pressures are measured using a fluid filled catheter inserted into a carotid artery. Data are digitized and recorded using an ADI (supplier Advanced Digital Instruments) system. Three beats are averaged for each time point.

Figure 4:
FIG. 4 is a photograph showing an illustrative embodiment of the hemorrhagic region contained within the risk zone.

Analysis o/No-reflow, Risk and Hemorrhagic Zones, and Necrosis. The heart are sliced transversely into 6-8 sections. The slices are photographed under ultraviolet light to identify the region of no-reflow (see FIG. 3, panel B) and under halogen lighting to identify the area at risk (see FIG. 3, panel A) and the hemorrhagic area (see FIG. 4). The slices are then be incubated in a 1% solution of triphenyltetrazolium chloride (TTC) for approximately 15 minutes, immersed in formalin, and re-photographed in order to visualize the infarcts (see FIG. 3, panel C). Necrotic tissue fails to stain with TTC and appears white to pale yellow. Non-infarcted tissue stains brick red. The digital photographs are observed on a computer monitor. The areas of no-reflow, hemorrhage, ischemic and normally perfused regions, and the areas of necrotic and non-necrotic regions in each slice are digitized using Image J (supplier Rasband WS, Image J, National Institutes of Health. The areas in each slice are multiplied by the weight of the slice and the results will summed in order to obtain the mass of the no-reflow, risk and infarcted areas.

One slice from the center of the infarcted region containing necrotic and normal zones are examined by histology and any edema are scored semi-quantitatively (scale of 0-3+). All photographic measurements are performed by a trained individual that is blinded to the study protocol.

Sample Size, Exclusion Criteria and Data Analyses.

Initial sample sizes will consist of n=8 animals in each group. Exclusion criteria include: death occurring before reperfusion and the study is completed, or an ischemic risk zone of <10% of the left ventricle. Data analyses include excluding animals in each group with a regional myocardial blood flow >0.2 ml/min/g within the risk zone during CAO, and inclusion of animals in each group with a regional myocardial blood flow >0.2 ml/min/g within the risk zone during CAO.

Blood Samples Collection and Handling.

Venous whole blood samples are collected for pharmacokinetic (PK) analyses. Table 12 summarizes collection time points. Venous whole blood samples are collected for PK analyses at the time points specified below. For PK analysis samples 1 ml venous whole blood is collected using pre-chilled syringe into the pre-chilled BD Vacutainer® Plasma Separation Tubes (lavender top) containing (spray coated) K$_2$EDTA at the following time points: for Group 1, 2 and 4, approximately baseline, 29 to 30 mins of ischemia (before on-set of the reperfusion). and approximately 30, 60 and 180 mins post-reperfusion. For Group 3, approximately 15, 30, 90 and 180 mins post-reperfusion.

TABLE 12

Summary of Collection Time Points

| | Surgery prep and stabilization | Ischemia (30 mins) | | | Reperfusion (180 mins) | | | | | | | |
|---|---|---|---|---|---|---|---|---|---|---|---|---|
| | | 0 | 5 | 15 | 29 to 30 | 5 | 15 | 30 | 60 | 90 | 120 | 150 | 180 |
| For Group 1, 2 and 4, venous blood draw for PK analysis (~1 ml plasma collection) | x | | | | x | | x | x | | | | | x |
| For Group 3, venous blood draw for PK analysis (~1 ml plasma collection) | x | | | | | x | x | | x | | | | x |
| Temperature* | x | | x | x | x | x | x | x | x | x | x | x | x |
| HR* | x | | x | x | x | x | x | x | x | x | x | x | x |
| Hemodynamic data* (ABP) | x | | x | x | x | x | x | x | x | x | x | x | x |

The PK blood tubes is adequately and gently mixed and placed immediately into ice. Within 30 minutes of collection, samples are centrifuged at approximately 1500 up to, preferably, 2000×G for 15 min at ~4° C., following which two plasma aliquots (approximately 0.25 ml each) are removed and immediately placed into labelled screw-cap polypropylene tubes. Individual plasma samples are quick frozen over dry ice, stored frozen under conditions set to maintain ~70° C.±15° C., until further analysis.

Statistical Analysis Plan.

All data summaries and statistical analyses are performed using SAS (Version 9.3). Left ventricular weight, infarct size, area at risk, area of no-reflow and hemorrhage and blood flow are compared using analysis of variance. The differences among groups are to be determined by Tukey's test. Changes in hemodynamic variables over time are analyzed by analysis of variance (repeated measures). If an f-value of <0.05 is obtained for the animal model, differences among means are determined by the method of contrasts. Analysis of covariance (ANCOVA) will also be used to test for a group effect on the regression models of necrotic myocardium with risk, no-reflow, and hemorrhage zones, and collateral blood flow. Data are expressed as mean±SEM.

End Points.

Endpoint for the studies may include, but are not limited to, heart rate, systolic/diastolic arterial pressure, pathologic specimen areas and their respective ratios, area at risk zone, infarct mass, left ventricular mass, risk zone, no-reflow zone, hemorrhage zone, necrosis/infarct size, and edema.

Other aromatic-cationic peptides, for example, Phe-D-Arg-Phe-Lys-NH$_2$ or pharmaceutically acceptable salts thereof, such as acetate salt or trifluoroacetate salt, could be tested in a similar manner.

Figure 5:
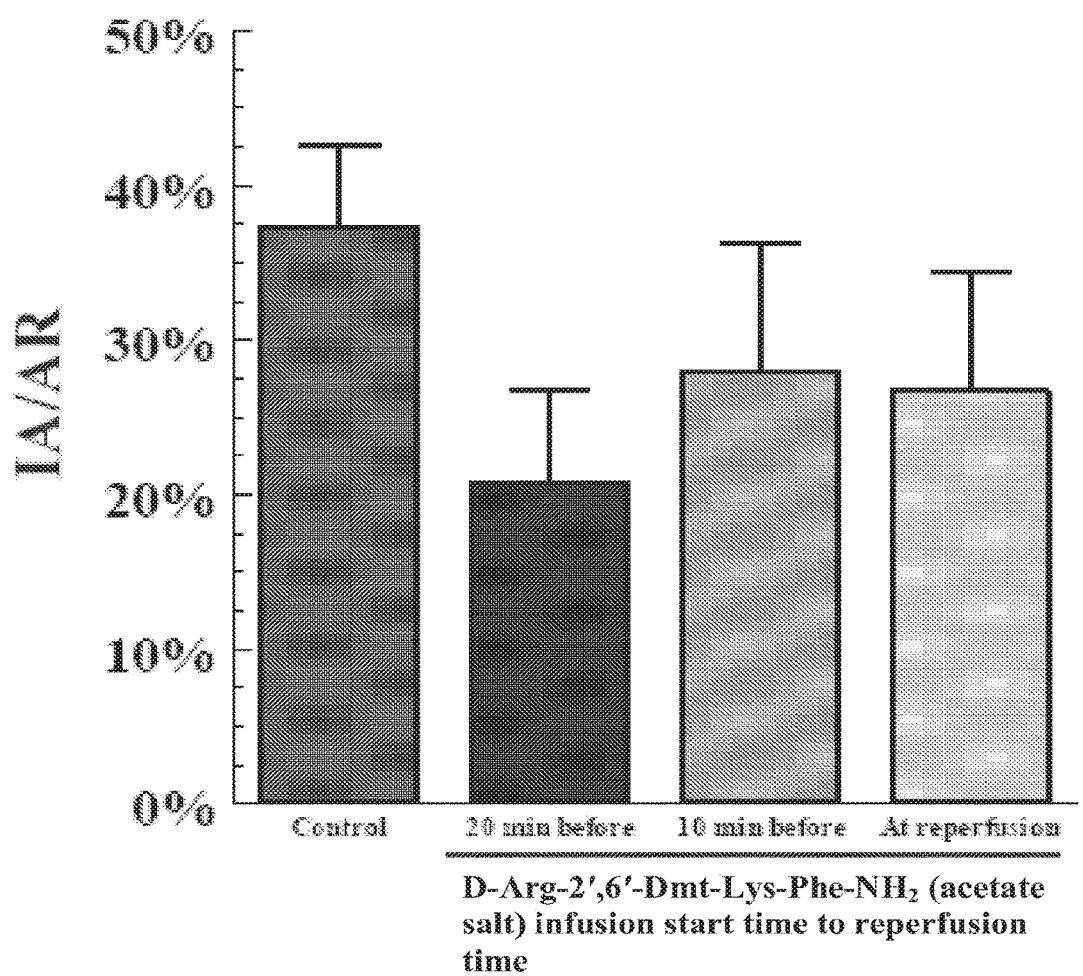
FIG. 5 is a graph showing the effect of D-Arg-2',6'-Dmt-Lys-Phe-NH$_2$ on the mean IA/AR in a rabbit model of AMI.

Example 2. Effect of D-Arg-2',6'-Dmt-Lys-Phe-NH_on the Mean IA/AR in a Rabbit Model of AMI Studies were conducted to assess the effect of D-Arg-2', 6'-Dmt-Lys-Phe-NH$_2$ on mean IA/AR in a rabbit model of AMI as described in Example 1. The effect of the timing of the infusion of D-Arg-2',6'-Dmt-Lys-Phe-NH$_2$ (acetate salt) was assessed. The effect of the timing of the infusion of D-Arg-2',6'-Dmt-Lys-Phe-NH$_2$ (acetate salt) at a low dose (from about 0.01 to about 0.5 mg/kg/h) was assessed. The results are shown in Table 13 and FIG. 5. D-Arg-2',6'-Dmt-Lys-Phe-NH$_2$ is useful in the treatment of ischemic injury as well as the prevention and treatment of reperfusion injury in heart as judged by a reduction in IA/AR ratio in subjects administered D-Arg-2',6'-Dmt-Lys-Phe-NH$_2$ (acetate salt) compared with subjects receiving placebo. In some experiments, the infarct size was reduced an average of 11% (not shown). In some experiments, the infarct size was reduced by up to 44.7% (Table 13; FIG. 5).

TABLE 13

Effect of D-Arg-2',6'-Dmt-Lys-Phe-NH$_2$ on Mean IA/AR in a Rabbit Model of AMI

| Treatment | Mean IA/AR | Results |
|---|---|---|
| Placebo | 37.4% | NA |
| D-Arg-2',6'-Dmt-Lys-Phe-NH$_2$ (acetate salt) (started 10 min into 30 min of ischemia | 20.7% | ↓44.7% from placebo |
| D-Arg-2',6'-Dmt-Lys-Phe-NH$_2$ (acetate salt) (started 20 min into 30 min of ischemia | 27.9% | ↓25.5% from placebo |
| D-Arg-2',6'-Dmt-Lys-Phe-NH$_2$ (acetate salt) (started 30 min into ischemia immediately prior to reperfusion) | 26.7% | ↓25.5% from placebo |

Other aromatic-cationic peptides, for example, Phe-D-Arg-Phe-Lys-NH$_2$ or pharmaceutically acceptable salts thereof, such as acetate salt or trifluoroacetate salt, could be tested in a similar manner. It is predicted that similar results would be achieved with the alternative peptides.

Example 3. Effects of D-Ara-2',6'-Dmt-Lys-Phe-NH$_2$ on the Anatomic Zone of No-Reflow, Zone of Hemorrhage and Infarct Size Following Ischemia/Reperfusion Insult in the Rabbit Heart Studies were conducted to assess the effect of D-Arg-2', 6'-Dmt-Lys-Phe-NH$_2$ on the anatomic zone of no-reflow, zone of hemorrhage and infarct size in a rabbit model of AMI as described in Example 1. The results show that D-Arg-2',6'-Dmt-Lys-Phe-NH$_2$ is useful in the treatment of ischemic injury as well as the prevention and treatment of reperfusion injury in heart, including an anatomical no re-flow zone.

Sixty-six rabbits entered the protocol which are inclusive of the animals detailed in Example 2. Data from two hearts were excluded based on the prospective exclusion criterion of ischemic risk zone size (AR<10% of the left ventricle). Final data are reported on the remaining 64 hearts: Group 1, n=15 (D-Arg-2',6'-Dmt-Lys-Phe-NH$_2$ (acetate salt) infusion starting at 10' after coronary artery occlusion [CAO]; Group 2, n=17 (D-Arg-2',6'-Dmt-Lys-Phe-NH$_2$ (acetate salt) infusion starting at 20' after CAO); Group 3, n=17 (D-Arg-2', 6'-Dmt-Lys-Phe-NH$_2$ (acetate salt) infusion starting at 29' after CAO); Group 4, n=15 (saline infusion starting at 10' after CAO). Three hearts had RMBF >0.20 ml/min/g in the ischemic zone during CAO; 3 rabbits may have had elevated serum levels of D-Arg-2',6'-Dmt-Lys-Phe-NH$_2$ due to issues with the infusion pump. These hearts were included in the data analyses presented here.

Ischemic risk zone, no-reflow zone, hemorrhagic zone and infarct size in the 4 groups is shown in Table 14. Mean and standard error values for these variables in the 4 group are provided. Potential differences among these variable were analyzed by analysis of variance.

TABLE 14

All hearts with AR >10% of the left ventricle

| | Group 1<br>N = 15<br>D-Arg-2',6'-<br>Dmt-Lys-Phe-<br>NH$_2$ (acetate<br>salt) 10' occl | Group 2<br>N = 17<br>D-Arg-2',6'-Dmt-<br>Lys-Phe-NH$_2$<br>(acetate salt) 20'<br>occl | Group 3<br>N = 17<br>D-Arg-2',6'-Dmt-<br>Lys-Phe-NH$_2$<br>(acetate salt) 29'<br>occl | Group 4<br>N = 15<br>saline |
|---|---|---|---|---|
| Area at risk/left ventricle | 0.30 ± 0.02 | 0.32 ± 0.02 | 0.31 ± 0.02 | 0.30 ± 0.02 |
| No-reflow/area at risk | 0.23 ± 0.02 | 0.21 ± 0.03 | 0.21 ± 0.03 | 0.28 ± 0.03 |
| No-reflow/area of necrosis | 0.74 ± 0.04 | 0.63 ± 0.05 | 0.70 ± 0.09 | 0.80 ± 0.05 |

Occl = coronary artery occlusion

Figure 6:
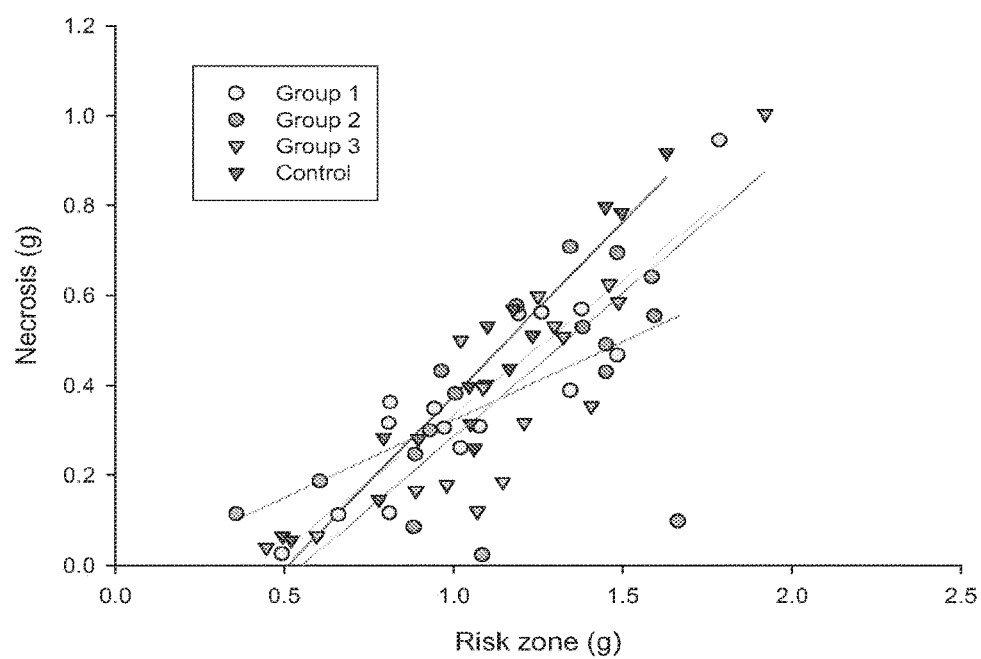
FIG. 6 is a graph showing the relationship between the necrotic zone and the risk zone in the treated and control groups in a rabbit model of AMI.
Figure 7:
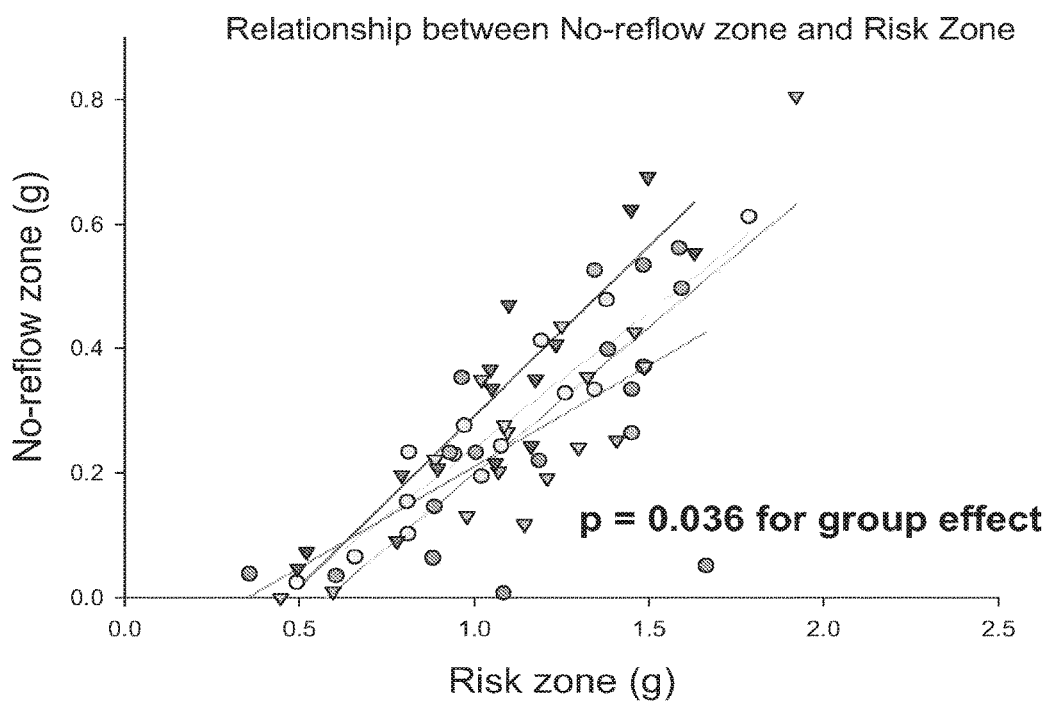
FIG. 7 is a graph showing the relationship between the risk zone and the no-reflow zone in the treated and control groups in a rabbit model of AMI.
Figure 9A:
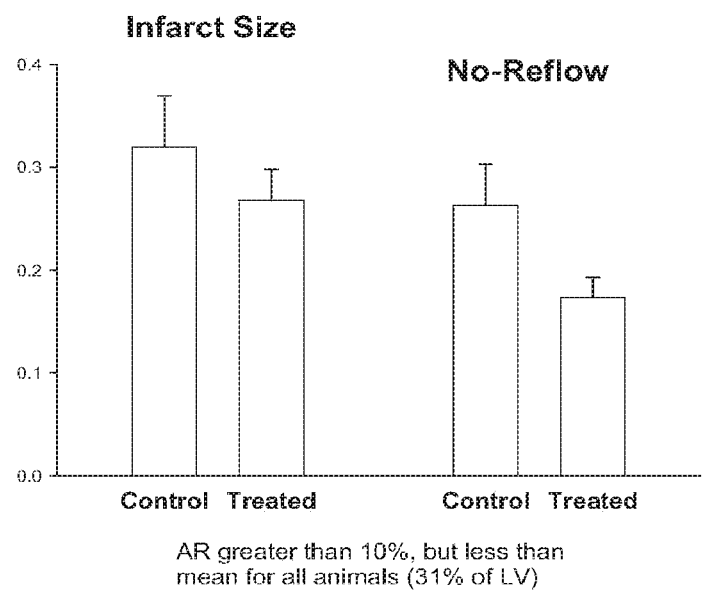
FIGS. 9A and 9B are graphs showing the infarct size and no-reflow zones in control and treated groups in a rabbit model of AMI.
Figure 9B:
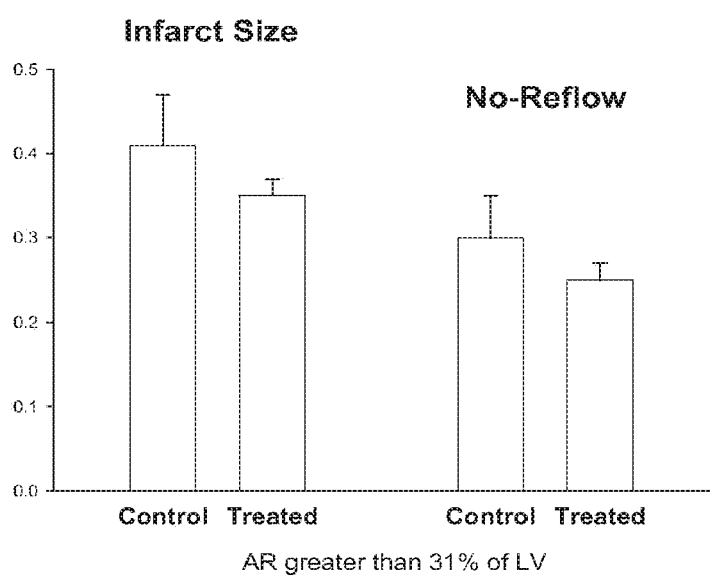

Analysis of Covariance was used to test the class variable "group" for an effect on the relationship between the extent of the risk region (AR/LV) expressed in grams and the extent of necrosis (AN/LV) (FIG. 6) and the extent of the risk region and that of the no-reflow region (FIG. 7). There was a significant effect of group on the relationship between no-reflow and risk. The regression lines for the treated groups lie below that of the control group. An analysis of the necrotic area divided by area-at-risk (AN/AR) for rabbits with AR/LV >15%, showed that treatment with D-Arg-2', 6'-Dmt-Lys-Phe-NH$_2$ results in a statistically significant reduction of infarct size of greater than 20% (See Table 15).

TABLE 15

Necrotic Area Divided By Area-At-Risk For Rabbits With AR/LV >15%

FOR ALL ACTIVE GROUPS COMBINED

| | |
|---|---|
| SUM | 15.245 |
| N | 48 |
| MEAN | 0.318 |
| REDUCTION IN AN/AR WITH D-Arg-2',6'-Dmt-Lys-Phe-NH$_2$ C/W PLACEBO | 20.2% |

ANCOVA testing for group effect was performed on the combined group data. There was a significant group effect on the relationship between the no-reflow zone and the risk zone (p=0.0085) (FIG. 8).

Regional Myocardial Blood Flow (RMBF) Data in the 4 Treatment Groups.

RMBF was measured in the ischemic region and the non-ischemic region at 25 minutes of coronary artery occlusion. In the preliminary data, there were 3 rabbits exhibiting non-ischemic values (>0.2 ml/min/g) in the ischemic risk zone. This may be due to the clamp gradually loosening over the course of the occlusion. In the second part of the study, a double-clamping method was used, and no hearts had a blood flow >0.2 ml/min/g in the ischemic region. Table 16 below shows RMBF values.

TABLE 16

RMBF (ml/min/g) with 3 hearts with ischemic flow >0.20 ml/min/g excluded

| | Ischemic Region | Non-ischemic Region |
|---|---|---|
| Group 1 | 0.02 ± 0.01 | 2.13 ± 0.12 |
| Group 2 | 0.03 ± 0.01 | 2.63 ± 0.29 |
| Group 3 | 0.05 ± 0.03 | 2.43 ± 0.19 |
| Control | 0.02 ± 0.01 | 2.32 ± 0.16 |

D-Arg-2',6'-Dmt-Lys-Phe-NH$_2$ treatment resulted in a trend of a 21% reduction in the extent of no-reflow compared with control hearts. There was a significant effect of the variable "group" on the relationship between the extent of the no-reflow zone and the extent of the risk region. This signal was even stronger when treated groups were combined and compared with control (p=0.0085).

In summary, for any given risk zone size, no-reflow was significantly reduced by D-Arg-2',6'-Dmt-Lys-Phe-NH$_2$, a finding that has important clinical implications. Recent studies show that worse no-reflow predicts worse LV dilation and remodeling in the chronic phase of infarction and is associated with worse prognosis, independent of changes in infarct size. See Reffelmann T et al. *Circulation* 2003; 108:2911-17; Wu K et al. *Circulation* 1998; 97:765-72; Ndrepepa et al. *J Am Coll Cardiol* 2010; 55:2383-89; and Bolognese et al. *Circulation* 2004; 109:1121-26. Because D-Arg-2',6'-Dmt-Lys-Phe-NH$_2$ reduces no-reflow for an average given risk zone size, we would predict that it will hasten healing (better removal of necrotic debris and better access to blood elements needed for healing) and thus reduce LV remodeling (including reducing LV dilation and LV eccentric hypertrophy). In addition, it will likely long-term survival.

Other aromatic-cationic peptides as disclosed herein, for example, Phe-D-Arg-Phe-Lys-NH$_2$ or pharmaceutically acceptable salts thereof, such as acetate salt or trifluoroacetate salt, could be tested and used in a similar manner, and it is predicted that similar results would be achieved.

Example 4. Effects of D-Ara-2',6'-Dmt-Lys-Phe-NH$_2$ on the Anatomic Zone of No-Reflow Following Ischemia/Reperfusion Insult in the Brain The effects of the aromatic-cationic peptides of the invention in protecting a subject from an anatomic zone of no-reflow caused by ischemia-reperfusion are investigated in an animal model of cerebral ischemia-reperfusion injury.

Cerebral ischemia initiates a cascade of cellular and molecular events that lead to brain damage. One such event is an anatomic zone of no-reflow. Cerebral ischemia is induced by occlusion of the right middle cerebral artery for 30 min. Wild-type (WT) mice are given either saline vehicle (Veh) (ip) or D-Arg-2',6'-Dmt-Lys-Phe-NH$_2$ (acetate salt) (2-5 mg/kg) at 0, 6, 24 and 48 h after ischemia. Mice are killed 3 days after ischemia. The brains are sliced transversely into 6-8 sections. The slices are photographed under ultraviolet light to identify the region of no-reflow. The areas of no-reflow in each slice are digitized using Image J (supplier Rasband WS, Image J, National Institutes of Health. The areas in each slice are multiplied by the weight of the slice and the results will summed in order to obtain the mass of the no-reflow areas.

Using a mouse model of cerebral ischemia-reperfusion (20 min. occlusion of the middle cerebral artery), it is predicted that treatment of wild type mice with D-Arg-2',6'-Dmt-Lys-Phe-NH$_2$ will result in a significant reduction in infarct volume and prevent or reduce the anatomic zone of no-reflow. As such, the peptide D-Arg-2',6'-Dmt-Lys-Phe-NH$_2$ is effective in reducing the incidence of no-reflow caused by ischemia-reperfusion in the brain.

Other aromatic-cationic peptides as disclosed herein, for example, Phe-D-Arg-Phe-Lys-NH$_2$ or pharmaceutically acceptable salts thereof, such as acetate salt or trifluoroacetate salt, could be tested and used in a similar manner. It is predicted that similar results would be achieved with the alternative aromatic-cationic peptides.

Example 5. Effects of D-Arg-2',6'-Dmt-Lys-Phe-NH$_2$ on the Anatomic Zone of No-Reflow Following Ischemia/Reperfusion Insult in the Kidney The effects of the aromatic-cationic peptides of the invention in protecting a subject from an anatomic zone of no-reflow caused by ischemia-reperfusion are investigated in an animal model of renal injury.

Sprague Dawley rats (250-300 g) are assigned to three groups: (1) sham surgery group without I/R; (2) I/R+ saline vehicle treatment; (3) I/R+D-Arg-2',6'-Dmt-Lys-Phe-NH$_2$ (acetate salt) treatment. D-Arg-2',6'-Dmt-Lys-Phe-NH$_2$ (acetate salt) (3 mg/kg, dissolved in saline) is administered to rats 30 min before ischemia and immediately before onset of reperfusion. The control rats are given saline alone on the same schedule. Rats are anesthetized with a mixture of ketamine (90 mg/kg, i.p.) and xylazine (4 mg/kg, i.p.). The left renal vascular pedicle is occluded temporarily using a micro-clamp for 30 or 45 min. At the end of the ischemic period, reperfusion is established by removing of the clamp. At that time, the contralateral right kidney is removed. After 24 h reperfusion, animals are sacrificed and blood samples were obtained by cardiac puncture. Renal function is determined by blood urea nitrogen (BUN) and scrum creatinine (BioAssay Systems DIUR-500 and DICT-500).

Analysis of No-Reflow Zones, and Necrosis.

The kidneys are sliced transversely into 6-8 sections. The slices are photographed under ultraviolet light to identify the region of no-reflow. The areas of no-reflow in each slice are digitized using Image J (supplier Rasband WS, Image J, National Institutes of Health. The areas in each slice are multiplied by the weight of the slice and the results will summed in order to obtain the mass of the no-reflow areas.

It is predicted that treatment with D-Arg-2',6'-Dmt-Lys-Phe-NH$_2$ prevents or reduces the anatomic zone of no-reflow after 45 min ischemia and 24 h reperfusion. For example, it is predicted that one or more of BUN, serum creatinine and glomerular filtration rate will be improved in subjects treated with the aromatic-cationic peptide as compared to subjects that did not receive the peptide treatment. As such, the peptide D-Arg-2',6'-Dmt-Lys-Phe-NH$_2$ is effective in reducing the incidence of no-reflow caused by ischemia-reperfusion in the kidney.

Other aromatic-cationic peptides, for example, Phe-D-Arg-Phe-Lys-NH$_2$ or pharmaceutically acceptable salts thereof, such as acetate salt or trifluoroacetate salt, could be tested and used in a similar manner. It is predicted that similar results would be achieved with the alternative aromatic-cationic peptides.

Example 6—Effects of Aromatic Cationic Peptides in Protecting Against the No-Reflow Phenomenon in Humans These studies will determine whether the administration of D-Arg-2',6'-Dmt-Lys-Phe-NH$_2$ at the time of revascularization would limit the size of an anatomic zone of no-reflow that occurs upon reperfusion. For treatment of AMI, the use of mechanical recanalization of the culprit artery restores epicardial coronary blood flow to ischemic myocardium (TIMI Flow Grade 3) in more than 90% of patients. However, these reperfusion efforts do not address the important ancillary problem of restoration of blood flow downstream at the level of the capillary bed. During or following primary PCI, microcirculatory dysfunction is observed in 20-40% of patients. The lack of ST-segment elevation resolution after angioplasty with stenting is a marker of microvascular problems and is associated with a poor clinical prognosis. In STEMI, failure to achieve myocardial reperfusion despite the presence of a patent coronary artery has been called the "no-reflow" phenomenon.

Study Group.

Men and women, 18 years of age or older, who present within 6 hours after the onset of chest pain, who have ST-segment elevation of more than 0.1 mV in two contiguous leads, and for whom the clinical decision is made to treat with percutaneous coronary intervention (PCI) are eligible for enrollment. Patients are eligible for the study whether they are undergoing primary PCI or rescue PCI. Occlusion of the culprit coronary artery (Thrombolysis in Myocardial Infarction [TIMI] flow grade 0) at the time of admission is also a criterion for inclusion.

Angiography and Revascularization.

Left ventricular and coronary angiography is performed with the use of standard techniques, just before revascularization. Revascularization is performed by PCI with the use of direct stenting. Alternative revascularization procedures include, but are not limited to, balloon angioplasty; insertion of a bypass graft; percutaneous transluminal coronary angioplasty, and directional coronary atherectomy Experimental Protocol.

After coronary angiography is performed but before the stent is implanted, patients who meet the enrollment criteria are randomly assigned to either the control group or the peptide group. Randomization is performed with the use of a computer-generated randomization sequence. Less than 10 min before direct stenting, the patients in the peptide group receive an intravenous bolus injection of D-Arg-2',6'-Dmt-Lys-Phe-NH$_2$ (acetate salt). The peptic is dissolved in normal saline (final concentration, 25 mg per milliliter) and is injected through a catheter that is positioned within an antecubital vein. The patients in the control group receive an equivalent volume of normal saline.

No-Reflow Zone.

The primary end point is the size of the anatomic zone of no-reflow as assessed by one or more imaging techniques. Re-flow phenomenon is assessed using myocardial contrast echocardiography, coronary angiography, myocardial blush, coronary doppler imaging, electrocardiograpy, nuclear imaging single-photon emission CT, using thallium or technetium-99m, or PET. A 1.5-T body MRI scanner is used to perform cardiac MRI in order to assess ventricular function, myocardial edema (area at risk), microvascular obstruction and infarct size. Post-contrast delayed enhancement is used on day 4±1, day 30±3 and 6+1.5 months after successful PCI and stenting to quantify infracted myocardium. This is defined quantitatively by an intensity of the myocardial post-contrast signal that is more than 2 SD above that in a reference region of remote, non-infarcted myocardium within the same slice. Standard extracellular gadolinium-based contrast agents is used at a dose of 0.2 mmol/kg. The 2D inversion recovery prepared fast gradient echo sequences is used at the following time points: (1) Early (approximately 2 minutes after contrast injection) for evaluation of microvascular obstruction. Single shot techniques may be considered if available and (2) Late (approximately 10 minutes after contrast injection) for evaluation of infarct size.

It is predicted that administration of the D-Arg-2',6'-Dmt-Lys-Phe-NH$_2$ (acetate salt) at the time of reperfusion will be associated with a smaller anatomic zone of no-reflow than that seen with placebo. As such, the peptide D-Arg-2',6'-Dmt-Lys-Phe-NH$_2$ is effective in reducing the incidence of no-reflow caused by ischemia-reperfusion in the heart.

Other aromatic-cationic peptides, for example, Phe-D-Arg-Phe-Lys-NH$_2$, or pharmaceutically acceptable salts thereof, such as acetate salt or trifluoroacetate salt, could be tested and used in a similar manner; it is predicted that similar results would be achieved.

REFERENCES

1. Ito H et al. (1996) Clinical implications of the 'no re-flow' phenomenon. A predictor of complications and left ventricular remodeling in reperfused anterior wall myocardial infarction. *Circulation* 93: 223-228.
2. Kloner R A et al. (1974) The "no-reflow" phenomenon after temporary coronary occlusion in the dog. *J Clin Invest* 54: 1496-1508.
3. Kloner R A et al. (1980) Ultrastructural evidence of microvascular damage and myocardial cell injury after coronary artery occlusion: which comes first? *Circulation* 62: 945-952.
4. Komamura K et al. (1994) Progressive decreases in coronary vein flow during reperfusion in acute myocardial infarction: clinical documentation of the no re-flow phenomenon after successful thrombolysis. *J Am Coll Cardiol* 24: 370-377.
5. Manciet L H et al. (1994) Microvascular compression during myocardial ischemia: mechanistic basis for no-reflow phenomenon. *Am J Physiol* 266: H1541-H1550.
6. Topol E J et al. (2000) Recognition of the importance of embolization in atherosclerotic vascular disease. *Circulation* 101: 570-580.
7. Fuster V et al. (1992) The pathogenesis of coronary artery disease and the acute coronary syndromes (1). *N Engl J Med* 326: 242-250.
8. Iwakura K et al. (2001) Predictive factors for development of the no-reflow phenomenon in patients with reperfused anterior wall acute myocardial infarction. *J Am Coll Cardiol* 38: 472-477.
9. Coggins M P et al. (2001) Noninvasive prediction of ultimate infarct size at the time of acute coronary occlusion based on the extent and magnitude of collateral-derived myocardial blood flow. *Circulation* 104: 2471-2477.
10. Iwakura K et al. (2003) Association between hyperglycemia and the no-reflow phenomenon in patients with acute myocardial infarction. *J Am Coll Cardiol* 41: 1-7.
11. Malmberg K et al. (1999) Glycometabolic state at admission: important risk marker of mortality in conventionally treated patients with diabetes mellitus and acute myocardial infarction: long-term results from the Diabetes and Insulin-Glucose Infusion in Acute Myocardial Infarction (DIGAMI) study. *Circulation* 99: 2626-2632.
12. Tanaka A et al. (2002) No-reflow phenomenon and lesion morphology in patients with acute myocardial infarction. *Circulation* 105: 2148-2152.
13. Kotani J et al. (2002) Plaque gruel of atheromatous coronary lesion may contribute to the no-reflow phenomenon in patients with acute coronary syndrome. *Circulation* 106: 1672-1677.
14. Hori M et al. (1986) Role of adenosine in hyperemic response of coronary blood flow in microembolization. *Am J Physiol* 250: H509-H518.
15. Okamura A et al. (2005) Detection of embolic particles with the Doppler guide wire during coronary intervention in patients with acute myocardial infarction: efficacy of distal protection device. *J Am Coll Cardiol* 45: 212-215.
16. Ito H et al. (1992) Lack of myocardial perfusion immediately after successful thrombolysis. A predictor of poor recovery of left ventricular function in anterior myocardial infarction. *Circulation* 85: 1699-1705.
17. Villanueva F S et al. (1993) Characterization of spatial patterns of flow within the reperfused myocardium by myocardial contrast echocardiography. Implication in determining extent of myocardial salvage. *Circulation* 88: 2596-2606.
18. Yano A et al. (2004) Myocardial contrast echocardiography with a new calibration method can estimate myocardial viability in patients with myocardial infarction. *J Am Coll Cardiol* 43: 1799-1806.
19. Zijlstra F et al. (1993) A comparison of immediate coronary angioplasty with intravenous streptokinase in acute myocardial infarction. *N Engl J Med* 328: 680-684.
20. Simes R J et al. (1995) Link between the angiographic substudy and mortality outcomes in a large randomized trial of myocardial reperfusion. Importance of early and complete infarct artery reperfusion. GUSTO-I Investigators. *Circulation* 91: 1923-1928.
21. Ito H et al. (1996) Myocardial perfusion patterns related to thrombolysis in myocardial infarction perfusion grades after coronary angioplasty in patients with acute anterior wall myocardial infarction. *Circulation* 93:1993-1999.

22. Grines C L et al. (1999) Coronary angioplasty with or without stent implantation for acute myocardial infarction. Stent Primary Angioplasty in Myocardial Infarction Study Group. *N Engl J Med* 341: 1949-1956.
23. Gibson C M et al. (2000) Relationship of TIMI myocardial perfusion grade to mortality after administration of thrombolytic drugs. *Circulation* 101: 125-130.
24. Iwakura K et al. (1996) Alternation in the coronary blood flow velocity pattern in patients with no re-flow and reperfused acute myocardial infarction. *Circulation* 94: 1269-1275.
25. Akasaka T et al. (2000) Relation of phasic coronary flow velocity characteristics with TIMI perfusion grade and myocardial recovery after primary percutaneous transluminal coronary angioplasty and rescue stenting. *Circulation* 101: 2361-2367.
26. Yamamoto K et al. (2002) Two different coronary blood flow velocity patterns in thrombolysis in myocardial infarction flow grade 2 in acute myocardial infarction: insight into mechanisms of microvascular dysfunction. *J Am Coll Cardiol* 40: 1755-1760.
27. Wehrens X et al. (2000) A comparison of electrocardiographic changes during reperfusion of acute myocardial infarction by thrombolysis or percutaneous transluminal coronary angioplasty. *Am Heart J* 139: 430-436.
28. Claeys M J et al. (1999) Determinants and prognostic implications of persistent ST-segment elevation after primary angioplasty for acute myocardial infarction: importance of microvascular reperfusion injury on clinical outcome. *Circulation* 99: 1972-1977.
29. Wu K C et al. (1998) Prognostic significance of microvascular obstruction by magnetic resonance imaging in patients with acute myocardial infarction. *Circulation* 97: 765-772.
30. Taylor A J et al. (2004) Detection of acutely impaired microvascular reperfusion after infarct angioplasty with magnetic resonance imaging. *Circulation* 109: 2080-2085.
31. Ito H et al (1996) Clinical implications of the 'no re-flow' phenomenon. A predictor of complications and left ventricular remodeling in reperfused anterior wall myocardial infarction. *Circulation* 93: 223-228.
32. Morishima I et al. (2000) Angiographic no-reflow phenomenon as a predictor of adverse long-term outcome in patients treated with percutaneous transluminal coronary angioplasty for first acute myocardial infarction. *J Am Coll Cardiol* 36: 1202-1209.
33. Kocher A A (2001) Neovascularization of ischemic myocardium by human bone marrow-derived angioblasts prevents cardiomyocyte apoptosis, reduces remodeling and improves cardiac function. *Nat Med* 7: 430-436.
34. Kunichika H et al. (2004) Effects of glycoprotein IIb/IIIa inhibition on microvascular flow after coronary reperfusion. A quantitative myocardial contrast echocardiography study. *J Am Coll Cardiol* 43: 276-283.
35. Montalescot G et al. (2001) Platelet glycoprotein IIb/IIIa inhibition with coronary stenting for acute myocardial infarction. *N Engl J Med* 344: 1895-1903.
36. Stone G W et al. (2005) Distal microcirculatory protection during percutaneous coronary intervention in acute ST-segment elevation myocardial infarction: a randomized controlled trial. *JAMA* 293: 1063-1072.
37. Gick M et al. (2005) Randomized evaluation of the effects of filter-based distal protection on myocardial perfusion and infarct size after primary percutaneous catheter intervention in myocardial infarction with and without ST-segment elevation. *Circulation* 112: 1462-1469.
38. Mizote I et al. (2005) Distal protection improved reperfusion and reduced left ventricular dysfunction in patients with acute myocardial infarction who had angioscopically defined ruptured plaque. *Circulation* 112: 1001-1007.
39. Makaryus A N et al. (2006) Efficacy of rheolytic thrombectomy in early versus late myocardial infarction. *J Interv Cardiol* 19: 135-140.
40. Ali A (2004) Rheolytic thrombectomy in patients with acute MI did not result in a reduction in myocardial infarct size. Presented at Transcatheter Cardiovascular Therapeutics: 2004 Sep. 27 to Oct. 1; Washington, D.C.
41. Tsang A et al. (2004) Postconditioning: a form of "modified reperfusion" protects the myocardium by activating the phosphatidylinositol 3-kinase-Akt pathway. *Circ Res* 95: 230-232.
42. Staat P et al. (2005) Postconditioning the human heart. *Circulation* 112: 2143-2148.
43. Marzilli M et al. (2000) Beneficial effects of intracoronary adenosine as an adjunct to primary angioplasty in acute myocardial infarction. *Circulation* 101: 2154-2159.
44. Ross A M et al. (2005) A randomized, double-blinded, placebo-controlled multicenter trial of adenosine as an adjunct to reperfusion in the treatment of acute myocardial infarction (AMISTAD-II). *J Am Coll Cardiol* 45: 1775-1780.
45. Ito H et al. (1999) Intravenous nicorandil can preserve microvascular integrity and myocardial viability in patients with reperfused anterior wall myocardial infarction. *J Am Coll Cardiol* 33: 654-660.
46. Ishii H et al. (2005) Impact of a single intravenous administration of nicorandil before reperfusion in patients with ST-segment-elevation myocardial infarction. *Circulation* 112: 1284-1288.
47. Taniyama Y (1997) Beneficial effect of intracoronary verapamil on microvascular and myocardial salvage in patients with acute myocardial infarction. *J Am Coll Cardiol* 30: 1193-1199.
48. Umemura S (2006) The effect of verapamil on the restoration of myocardial perfusion and functional recovery in patients with angiographic no-reflow after primary percutaneous coronary intervention. *Nucl Med Commun* 27: 247-254.
49. Pasceri V (2005) Effects of the nitric oxide donor nitroprusside on no-reflow phenomenon during coronary interventions for acute myocardial infarction. *Am J Cardiol* 95: 1358-1361.
50. Theroux P (2000) Myocardial cell protection: a challenging time for action and a challenging time for clinical research. *Circulation* 101: 2874-2876.
51. Theroux P et al. (2000) Inhibition of the sodium-hydrogen exchanger with cariporide to prevent myocardial infarction in high-risk ischemic situations. Main results of the GUARDIAN trial. Guard during ischemia against necrosis (GUARDIAN) Investigators. *Circulation* 102: 3032-3038.
52. Zeymer U et al. (2001) The Na+/H+ exchange inhibitor eniporide as an adjunct to early reperfusion therapy for acute myocardial infarction. Results of the evaluation of the safety and cardioprotective effects of eniporide in acute myocardial infarction (ESCAMI) trial. *J Am Coll Cardiol* 38: 1644-1650.
53. Cai Z and Semenza G L (2004) Phosphatidylinositol-3-kinase signaling is required for erythropoietin-mediated acute protection against myocardial ischemia/reperfusion injury. *Circulation* 109: 2050-2053.

EQUIVALENTS

The present invention is not to be limited in terms of the particular embodiments described in this application, which are intended as single illustrations of individual aspects of the invention. Many modifications and variations of this invention can be made without departing from its spirit and scope, as were apparent to those skilled in the art. Functionally equivalent methods and apparatuses within the scope of the invention, in addition to those enumerated herein, were apparent to those skilled in the art from the foregoing descriptions. Such modifications and variations are intended to fall within the scope of the appended claims. The present invention is to be limited only by the terms of the appended claims, along with the full scope of equivalents to which such claims are entitled. It is to be understood that this invention is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As were understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as were understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

Other embodiments are set forth within the following claims.

What is claimed is:

1. A method for treating a zone of hemorrhage in a mammalian subject in need thereof, the method comprising administering to the subject a therapeutically effective amount of a peptide D-Arg-2',6'-Dmt-Lys-Phe-NH$_2$ or a pharmaceutically acceptable salt thereof, thereby treating the zone of hemorrhage in the subject.

2. The method of claim 1, further comprising the step of performing a revascularization.

3. The method of claim 1, wherein the subject is suffering from a zone of hemorrhage associated with a tissue selected from the group consisting of cardiovascular tissue, skeletal muscle tissue, cerebral tissue, and renal tissue.

4. The method of claim 2, wherein the subject is administered the peptide prior to the revascularization procedure, after the revascularization procedure, during and after the revascularization procedure, or continuously before, during, and after the revascularization procedure.

5. The method of claim 4, wherein the subject is administered the peptide for at least 3 hours after the revascularization procedure, for at least 5 hours after the revascularization procedure, for at least 8 hours after the revascularization procedure, for at least 12 hours after the revascularization procedure, or for at least 24 hours after the revascularization procedure.

6. The method of claim 4, wherein the subject is administered the peptide starting at least 8 hours before the revascularization procedure, starting at least 4 hours before the revascularization procedure, starting at least 2 hours before the revascularization procedure, starting at least 1 hour before the revascularization procedure, or starting at least 10 minutes before the revascularization procedure.

7. The method of claim 1, wherein the subject is suffering from a myocardial infarction or a stroke, or is in need of angioplasty.

8. The method of claim 2, wherein the revascularization procedure is selected from the group consisting of balloon angioplasty, insertion of a bypass graft, insertion of a stent, percutaneous transluminal coronary angioplasty, and directional coronary atherectomy.

9. The method of claim 2, wherein the revascularization procedure is removal of an occlusion.

10. The method of claim 2, wherein the revascularization procedure is administration of one or more thrombolytic agents.

11. The method of claim 10, wherein the one or more thrombolytic agents are selected from the group consisting of tissue plasminogen activator, urokinase, prourokinase, streptokinase, acylated form of plasminogen, acylated form of plasmin, and acylated streptokinase-plasminogen complex.

* * * * *